(12) United States Patent
Henniges et al.

(10) Patent No.: US 10,426,536 B2
(45) Date of Patent: Oct. 1, 2019

(54) METHOD OF DELIVERING A PLURALITY OF ELEMENTS AND FLUENT MATERIAL INTO A VERTEBRAL BODY

(71) Applicant: Stryker Corporation, Kalamazoo, MI (US)

(72) Inventors: Bruce D. Henniges, Galesburg, MI (US); Richard F. Huyser, Kalamazoo, MI (US); Douglas L. Tyler, Paw Paw, MI (US)

(73) Assignee: STRYKER CORPORATION, Kalamazoo, MI (US)

(*) Notice: Subject to any disclaimer, the term of this patent is extended or adjusted under 35 U.S.C. 154(b) by 744 days.

(21) Appl. No.: 15/056,393

(22) Filed: Feb. 29, 2016

(65) Prior Publication Data

US 2016/0175019 A1    Jun. 23, 2016

Related U.S. Application Data

(62) Division of application No. 11/627,771, filed on Jan. 26, 2007, now Pat. No. 9,301,792.
(Continued)

(51) Int. Cl.
*A61B 17/88* (2006.01)
*A61B 17/34* (2006.01)
*A61B 17/70* (2006.01)

(52) U.S. Cl.
CPC ...... *A61B 17/8805* (2013.01); *A61B 17/3472* (2013.01); *A61B 17/7094* (2013.01);
(Continued)

(58) Field of Classification Search
CPC .................. A61F 2/4611; A61F 2/4455; A61F 2002/444; A61F 2002/4445; A61F 2/46;
(Continued)

(56) References Cited

U.S. PATENT DOCUMENTS

| 834,261 A | 10/1906 | Chambers |
| 1,347,622 A | 7/1920 | Deininger |

(Continued)

FOREIGN PATENT DOCUMENTS

| DE | 2320373 A1 | 11/1974 |
| DE | 2651441 C2 | 11/1976 |

(Continued)

OTHER PUBLICATIONS

PCT International Search Report and Written Opinion for PCT/US2007/002466, dated Jun. 28, 2007.

*Primary Examiner* — Matthew J Lawson
(74) *Attorney, Agent, or Firm* — Howard & Howard Attorneys PLLC

(57) ABSTRACT

A system for forming an implant to stabilize an interior of a vertebral body is provided. The system includes a delivery cannula. A plurality of elements are disposed adjacent to one another in the delivery cannula with void spaces defined between the elements. A fluent material, capable of setting to a hardened condition, is disposed within at least a portion of the void space in the delivery cannula. A push rod is movably disposed within the delivery cannula to apply a force to move the elements through the delivery cannula and into the interior of the vertebral body. Upon application of the force, the elements simultaneously carry the fluent material through the delivery cannula and into vertebral body to delivery the fluent material at a low pressure. The fluent material sets to the hardened condition to secure the elements and form the implant.

19 Claims, 20 Drawing Sheets

Related U.S. Application Data

(60) Provisional application No. 60/762,779, filed on Jan. 27, 2006, provisional application No. 60/808,681, filed on May 26, 2006.

(52) U.S. Cl.
CPC ...... *A61B 17/7095* (2013.01); *A61B 17/8811* (2013.01); *A61B 17/8816* (2013.01); *A61B 17/8822* (2013.01)

(58) Field of Classification Search
CPC ........... A61F 2/4601; A61F 2002/4602; A61B 17/8805; A61B 17/885; A61B 17/8855
USPC .................. 623/17.11–17.16; 606/92–94
See application file for complete search history.

(56) References Cited

U.S. PATENT DOCUMENTS

| | | |
|---|---|---|
| 1,596,754 A | 10/1923 | Moschelle |
| 2,526,735 A | 10/1950 | Duce |
| 2,659,369 A | 11/1953 | Lipman |
| 3,882,858 A | 5/1975 | Klemm |
| 4,191,740 A | 3/1980 | Huesser et al. |
| 4,270,675 A | 6/1981 | Wicks et al. |
| 4,341,691 A | 7/1982 | Anuta |
| 4,451,253 A | 5/1984 | Harman |
| 4,791,150 A | 12/1988 | Braden |
| 4,904,260 A | 2/1990 | Ray et al. |
| 5,004,260 A | 4/1991 | Smyly, Sr. |
| 5,113,871 A | 5/1992 | Viljanto et al. |
| 5,192,326 A | 3/1993 | Bao et al. |
| 5,288,291 A | 2/1994 | Teoh |
| 5,334,626 A | 8/1994 | Lin |
| 5,431,654 A | 7/1995 | Nic |
| 5,445,832 A | 8/1995 | Orsonlini et al. |
| 5,512,610 A | 4/1996 | Lin |
| 5,514,101 A | 5/1996 | Schulz et al. |
| 5,534,023 A | 7/1996 | Henley |
| 5,638,997 A | 6/1997 | Hawkins et al. |
| 5,641,514 A | 6/1997 | Cho |
| 5,681,279 A | 10/1997 | Roper et al. |
| 5,702,454 A | 12/1997 | Baumgartner |
| 5,718,707 A | 2/1998 | Mikhail |
| 5,755,797 A | 5/1998 | Baumgartner |
| 5,756,127 A | 5/1998 | Grisoni et al. |
| 5,797,882 A | 8/1998 | Purdy et al. |
| 5,893,488 A | 4/1999 | Hoag et al. |
| 5,958,465 A | 9/1999 | Klemm et al. |
| 5,997,580 A | 12/1999 | Mastrorio et al. |
| 6,139,320 A | 10/2000 | Hahn |
| 6,183,768 B1 | 2/2001 | Harle |
| 6,231,615 B1 | 5/2001 | Preissman |
| 6,241,734 B1 | 6/2001 | Scribner et al. |
| 6,280,477 B1 | 8/2001 | Mastrorio et al. |
| 6,309,420 B1 | 10/2001 | Preissman |
| 6,340,299 B1 | 1/2002 | Saito |
| 6,387,130 B1 | 5/2002 | Stone et al. |
| 6,595,998 B2 | 7/2003 | Johnson et al. |
| 6,613,054 B2 | 9/2003 | Scribner et al. |
| 6,620,162 B2 * | 9/2003 | Kuslich .............. A61B 17/7095 222/200 |
| 6,648,849 B2 | 11/2003 | Tenhuisen et al. |
| 6,719,761 B1 | 4/2004 | Reiley et al. |
| 6,939,318 B2 | 9/2005 | Stenzel |
| 6,960,183 B2 | 11/2005 | Nicolette |
| 7,025,771 B2 | 4/2006 | Kuslich et al. |
| 7,351,262 B2 | 4/2008 | Bindseil et al. |
| 7,682,400 B2 | 3/2010 | Zwirkoski |
| 7,803,188 B2 | 9/2010 | Justis et al. |
| 8,062,364 B1 | 11/2011 | Sharkey et al. |
| 8,551,178 B2 | 10/2013 | Sharkey et al. |
| 8,574,303 B2 | 11/2013 | Sharkey et al. |
| 8,608,802 B2 | 12/2013 | Bagga et al. |
| 8,617,166 B2 | 12/2013 | Hanson et al. |
| 8,623,089 B2 | 1/2014 | Sharkey et al. |
| 2001/0034527 A1 | 10/2001 | Scribner et al. |
| 2002/0068974 A1 | 6/2002 | Kuslich et al. |
| 2002/0183761 A1* | 12/2002 | Johnson ............... A61B 17/025 606/90 |
| 2003/0018292 A1 | 1/2003 | Kuslich et al. |
| 2003/0045597 A1 | 3/2003 | Randolph et al. |
| 2003/0191414 A1 | 10/2003 | Reiley et al. |
| 2004/0010260 A1 | 1/2004 | Scribner et al. |
| 2004/0010314 A1 | 1/2004 | Matsuzaki et al. |
| 2004/0019354 A1 | 1/2004 | Johnson et al. |
| 2004/0024409 A1 | 2/2004 | Sand et al. |
| 2004/0052829 A1 | 3/2004 | Shimp |
| 2004/0064136 A1 | 4/2004 | Papineau et al. |
| 2004/0064144 A1 | 4/2004 | Johnson et al. |
| 2004/0068234 A1 | 4/2004 | Martin et al. |
| 2004/0097930 A1* | 5/2004 | Justis ................. A61B 17/7094 606/86 A |
| 2004/0111053 A1 | 6/2004 | Nicolette |
| 2004/0215343 A1 | 10/2004 | Hochschuler et al. |
| 2004/0220580 A1 | 11/2004 | Johnson et al. |
| 2005/0015148 A1 | 1/2005 | Jansen et al. |
| 2005/0033265 A1 | 2/2005 | Engel et al. |
| 2005/0038517 A1 | 2/2005 | Carrison et al. |
| 2005/0070912 A1 | 3/2005 | Voellmicke |
| 2005/0070915 A1 | 3/2005 | Mazzuca et al. |
| 2005/0113843 A1 | 5/2005 | Arramon |
| 2005/0124999 A1 | 6/2005 | Teitelbaum et al. |
| 2005/0128867 A1 | 6/2005 | Henniges et al. |
| 2005/0128868 A1 | 6/2005 | Vries |
| 2005/0143688 A1 | 6/2005 | Lin et al. |
| 2005/0171522 A1 | 8/2005 | Christopherson |
| 2005/0182414 A1 | 8/2005 | Manzi et al. |
| 2005/0187558 A1 | 8/2005 | Johnson et al. |
| 2005/0216018 A1 | 9/2005 | Sennet |
| 2005/0228397 A1 | 10/2005 | Malandain et al. |
| 2005/0234493 A1 | 10/2005 | Carr et al. |
| 2005/0244451 A1 | 11/2005 | Diaz et al. |
| 2005/0251149 A1 | 11/2005 | Wenz |
| 2005/0278023 A1* | 12/2005 | Zwirkoski .......... A61B 17/7094 623/11.11 |
| 2006/0036273 A1 | 2/2006 | Siegal |
| 2006/0079905 A1 | 4/2006 | Beyar et al. |
| 2006/0085008 A1 | 4/2006 | Jaggi et al. |
| 2006/0085009 A1 | 4/2006 | Truckai et al. |
| 2006/0085081 A1 | 4/2006 | Shadduck et al. |
| 2006/0095138 A1 | 5/2006 | Truckai et al. |
| 2006/0100304 A1* | 5/2006 | Vresilovic ............... A61F 2/442 523/113 |
| 2006/0122624 A1 | 6/2006 | Truckai et al. |
| 2006/0184246 A1* | 8/2006 | Zwirkoski .......... A61B 17/7094 623/11.11 |
| 2006/0265077 A1 | 11/2006 | Zwirkoski |
| 2007/0093822 A1* | 4/2007 | Dutoit .................... A61B 17/68 606/258 |
| 2007/0162132 A1* | 7/2007 | Messerli ................ A61B 17/68 623/17.11 |
| 2007/0233146 A1 | 10/2007 | Henniges et al. |

FOREIGN PATENT DOCUMENTS

| | | |
|---|---|---|
| DE | 10309986 A1 | 9/2004 |
| GB | 2237564 A | 8/1991 |
| WO | 8203174 A1 | 9/1982 |
| WO | 198203174 A1 | 9/1982 |
| WO | 0054821 A1 | 9/2000 |
| WO | 2002047563 A1 | 6/2002 |
| WO | 2060504 A1 | 8/2002 |
| WO | 5094735 A3 | 10/2005 |

* cited by examiner

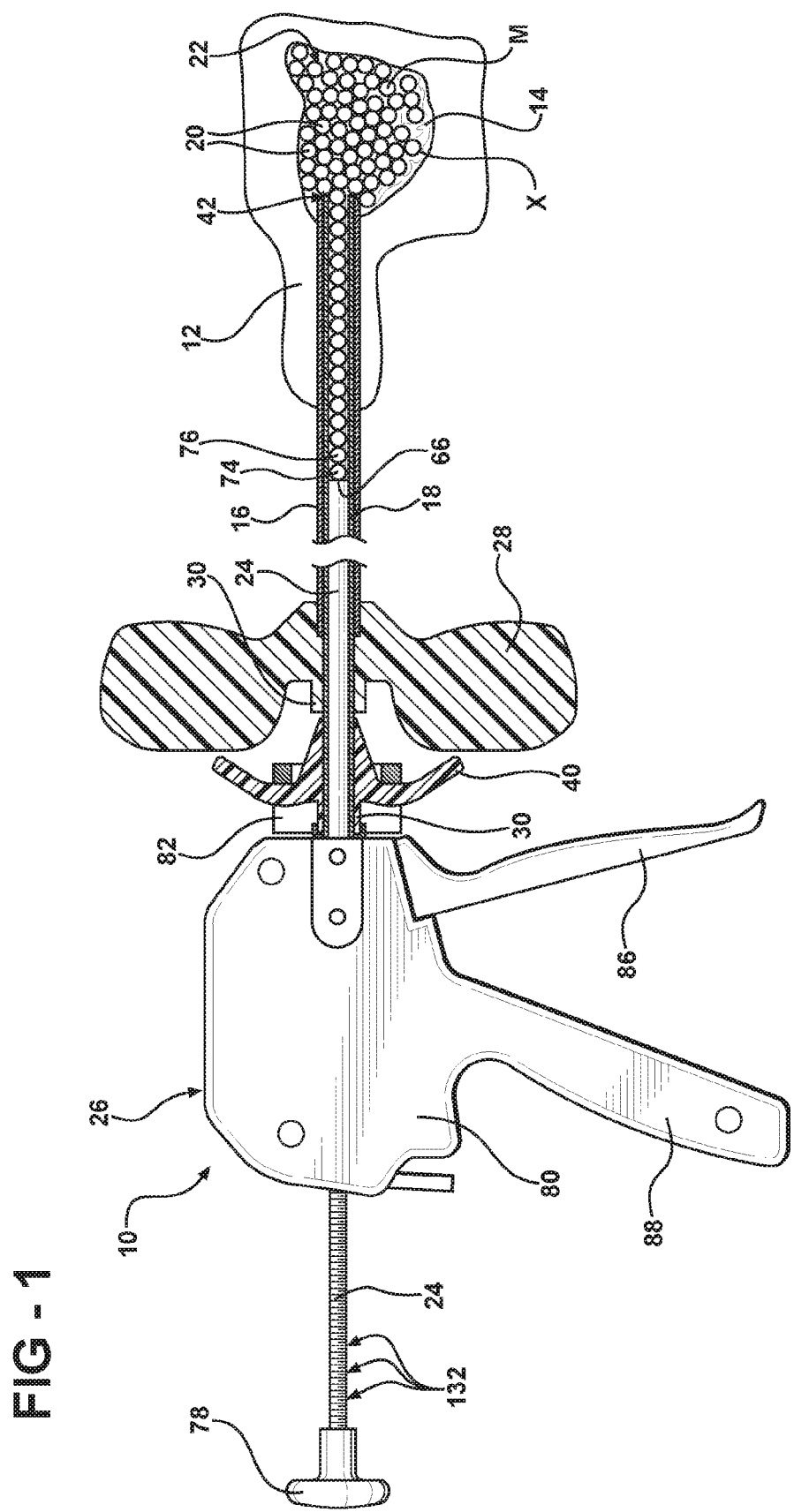

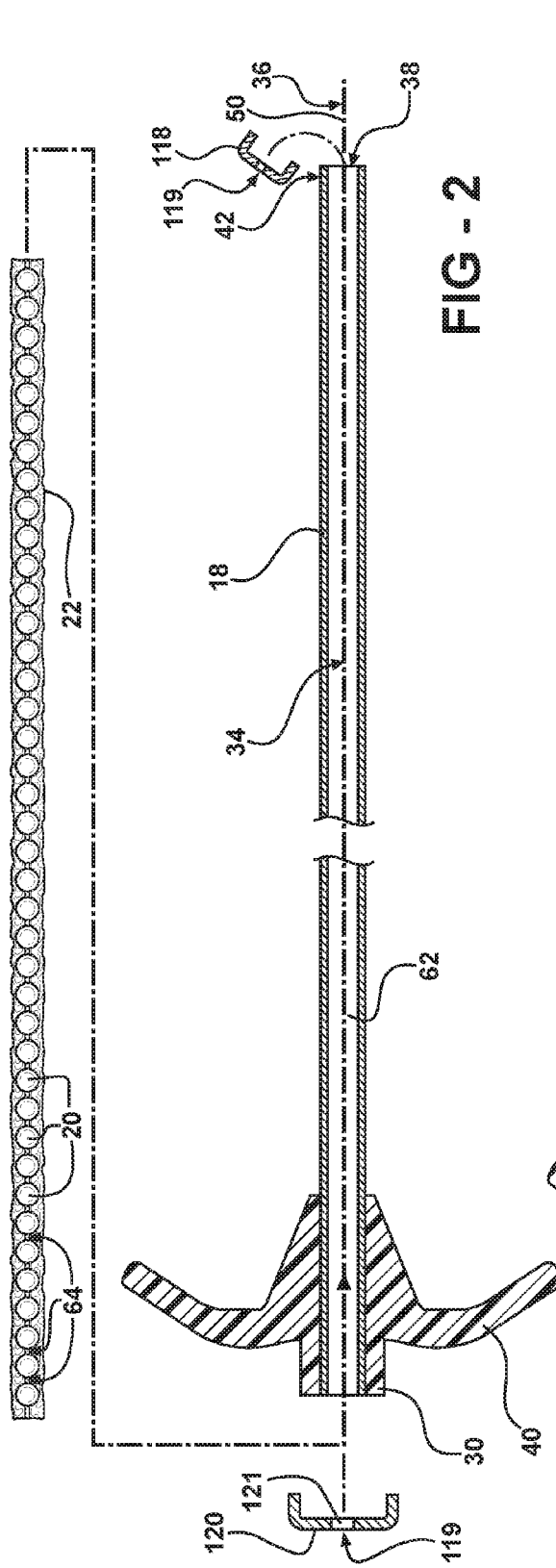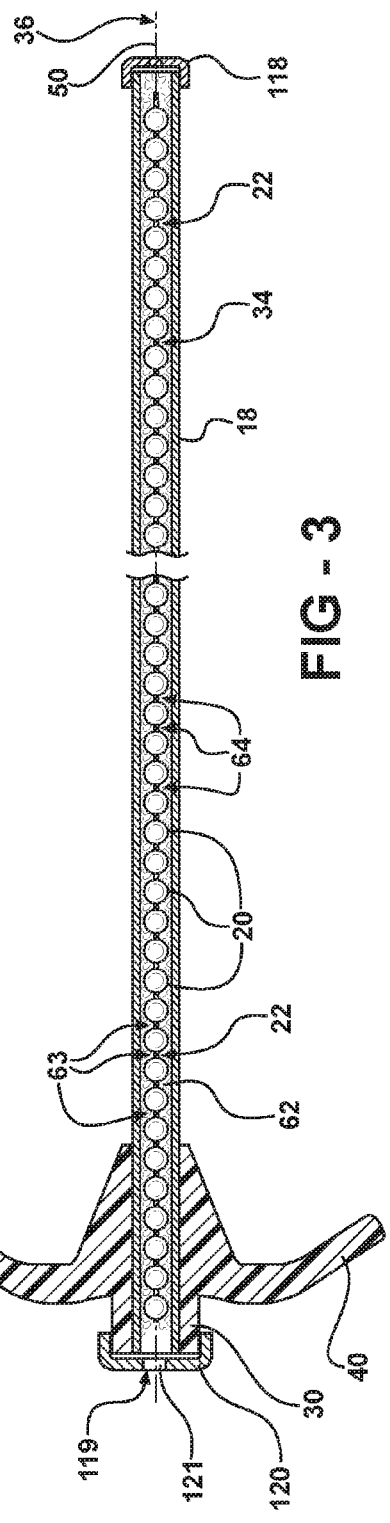

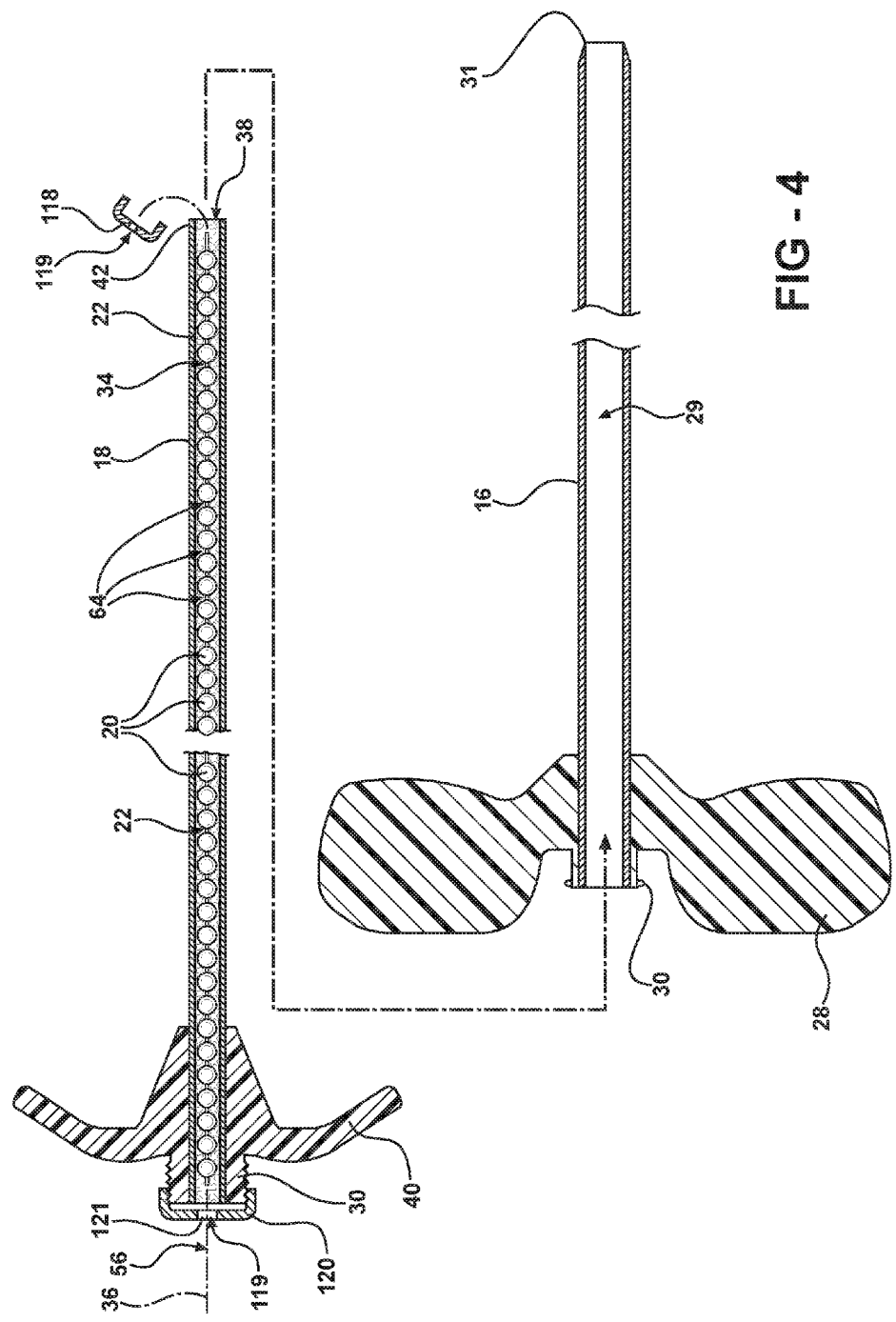

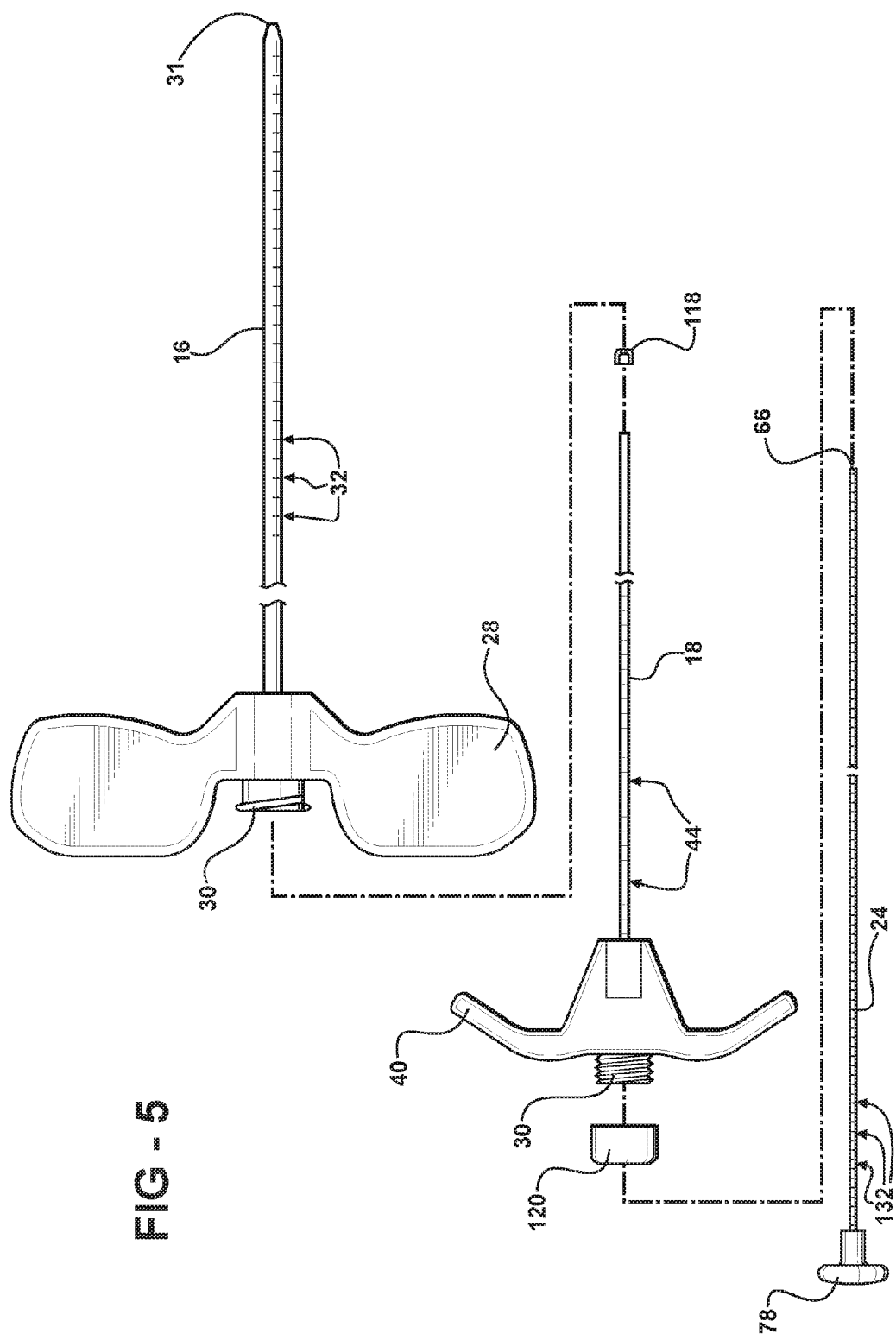

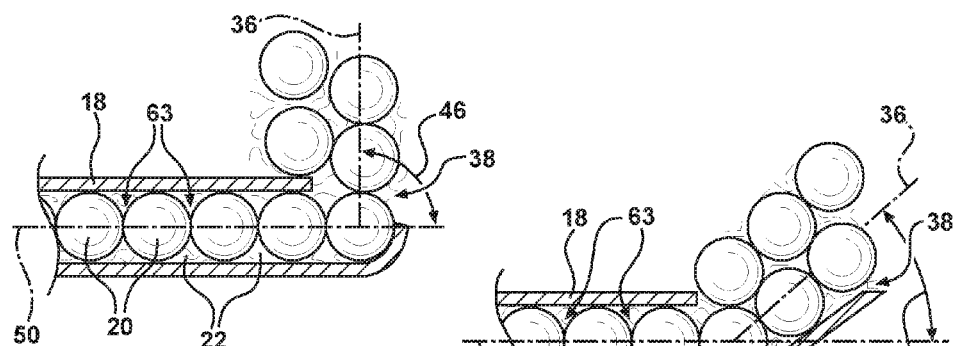
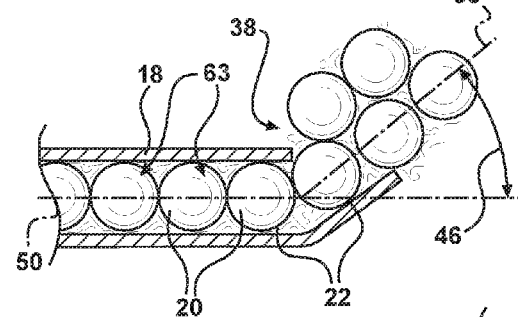
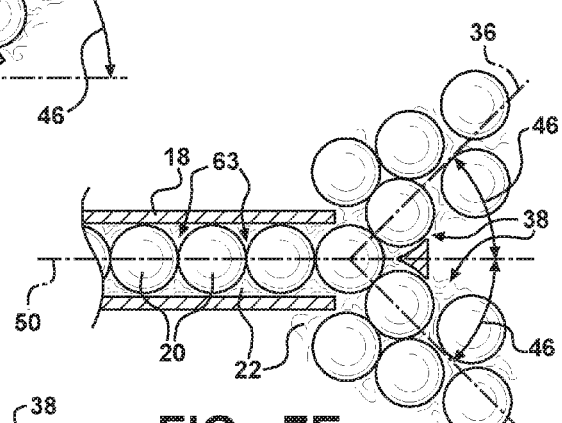
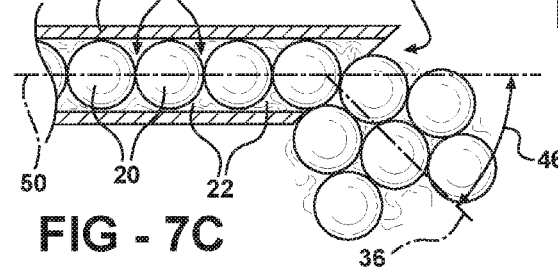
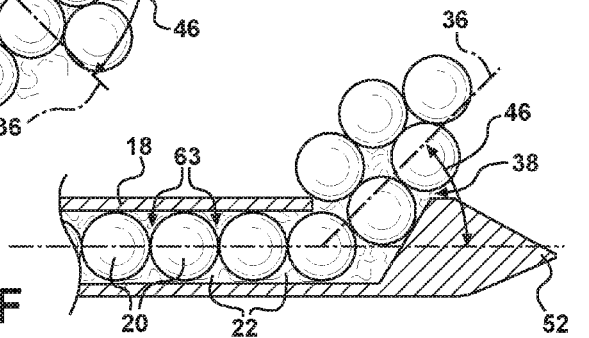

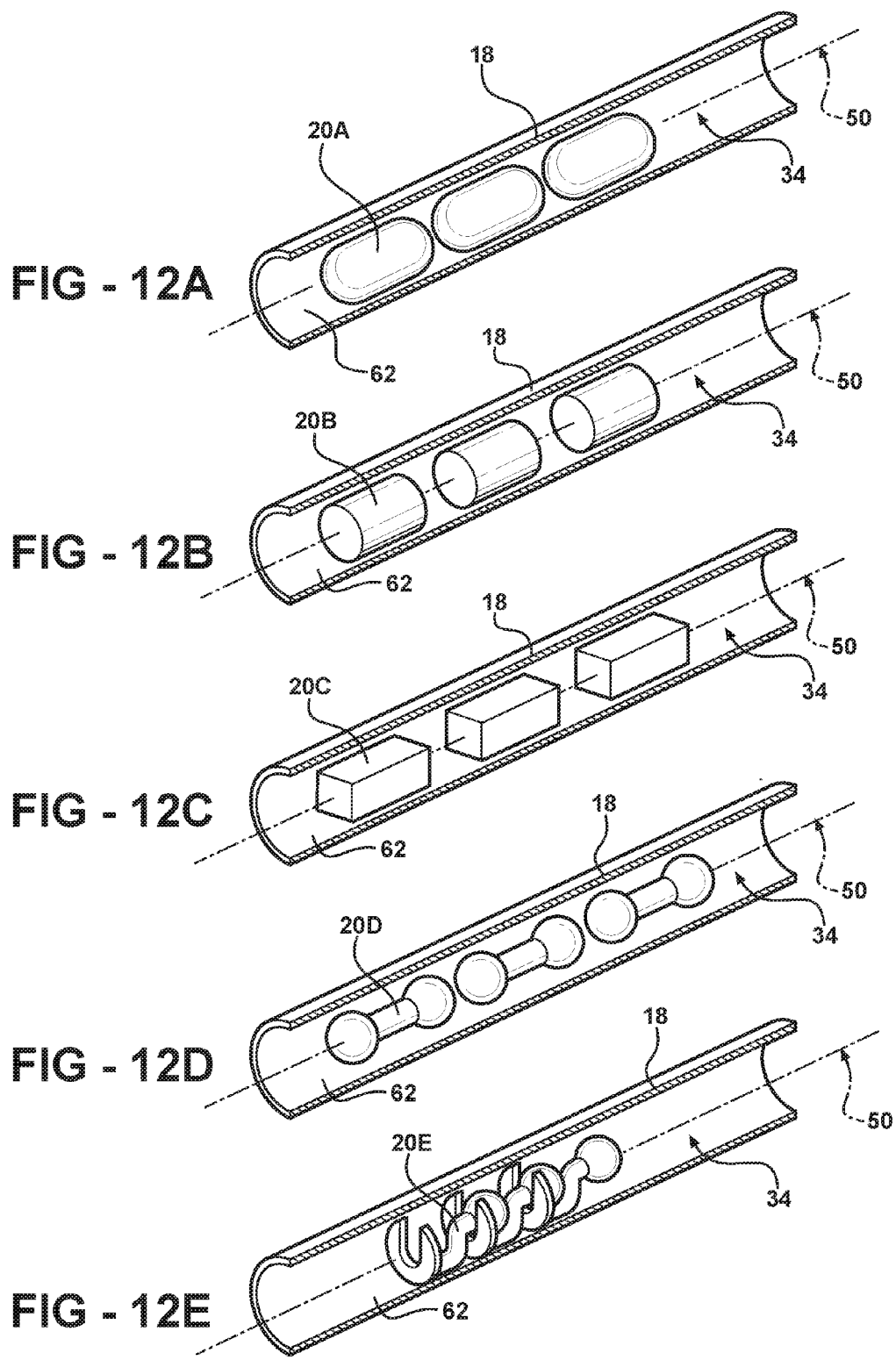

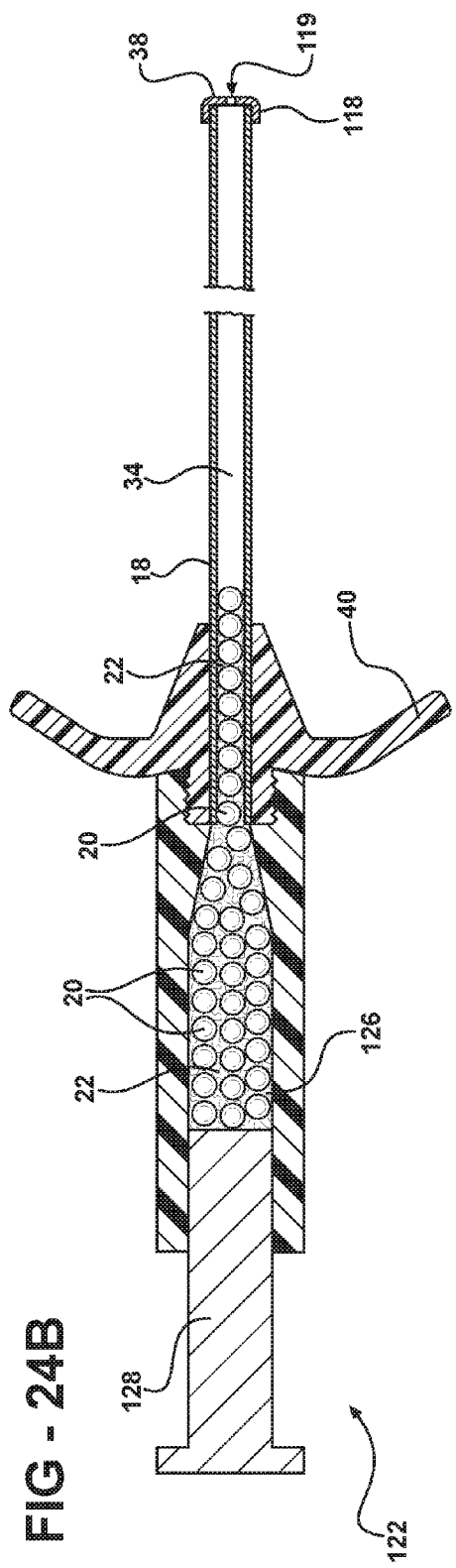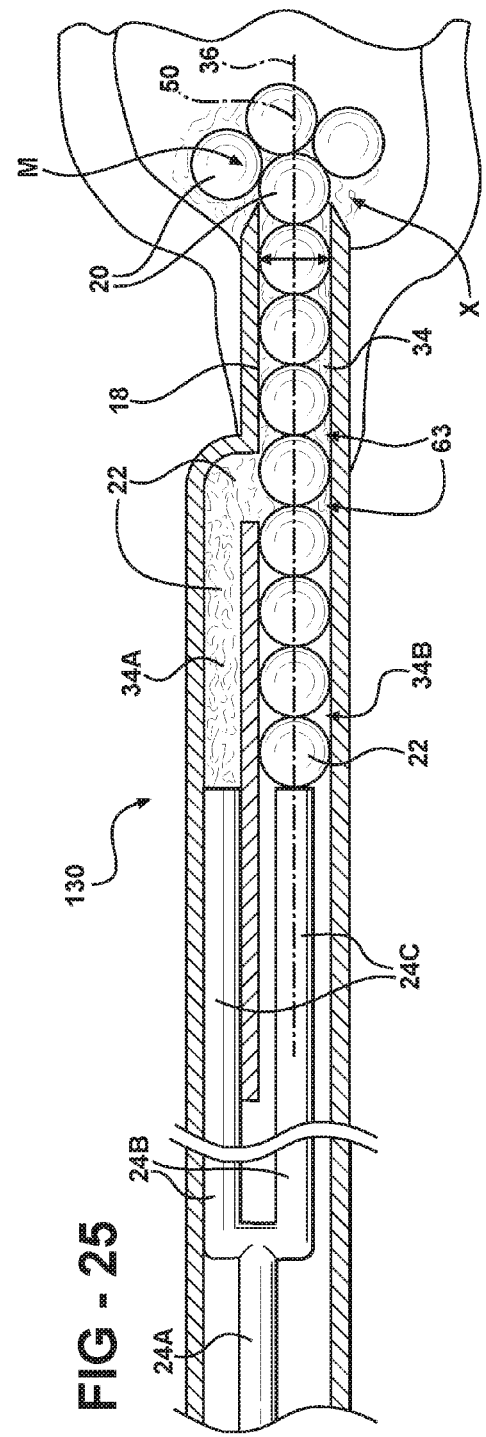

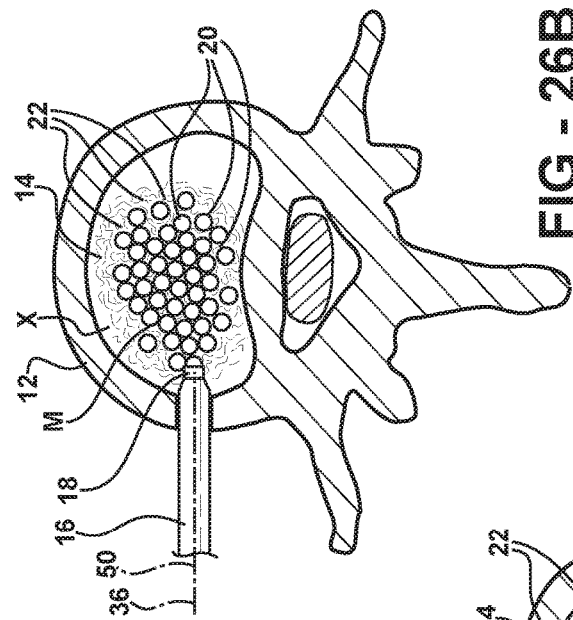
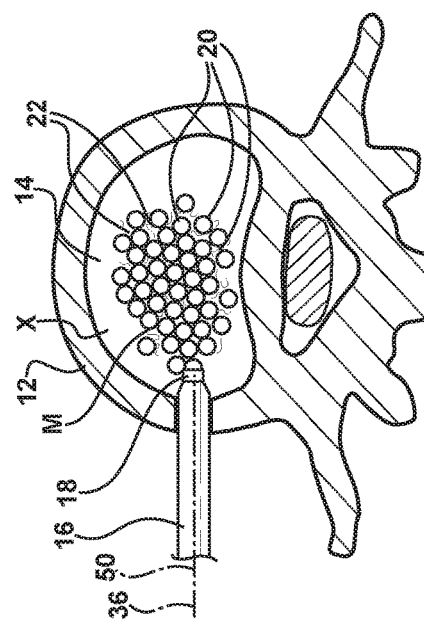
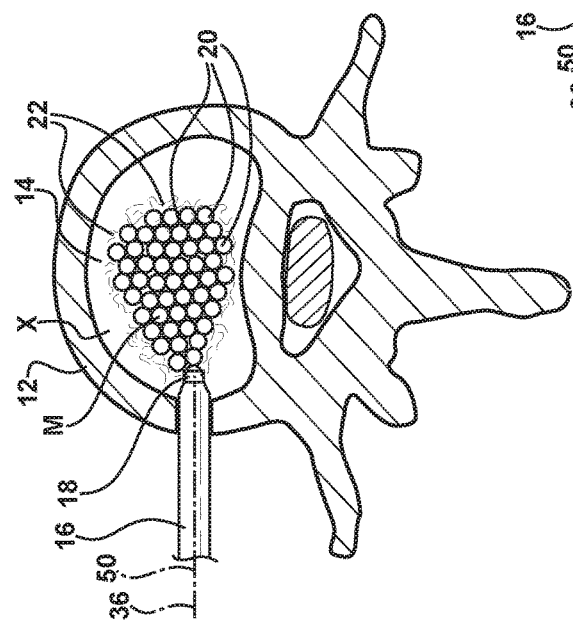

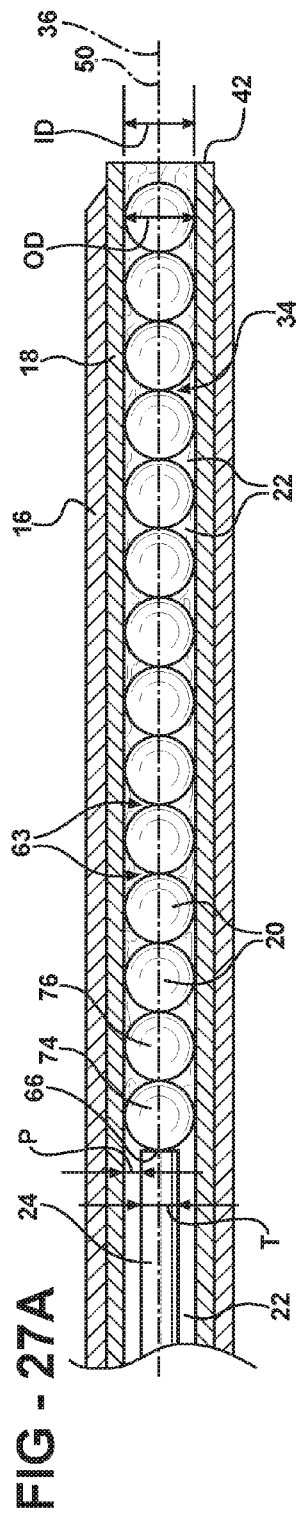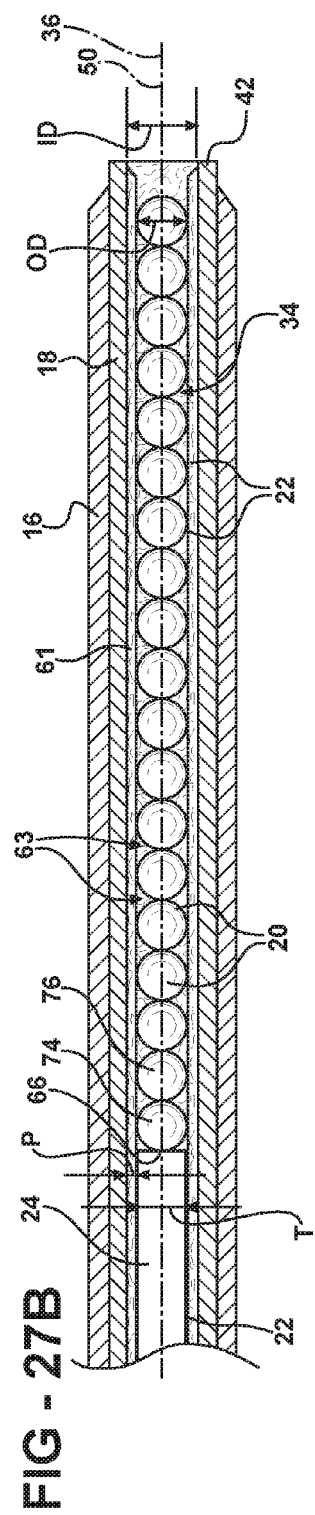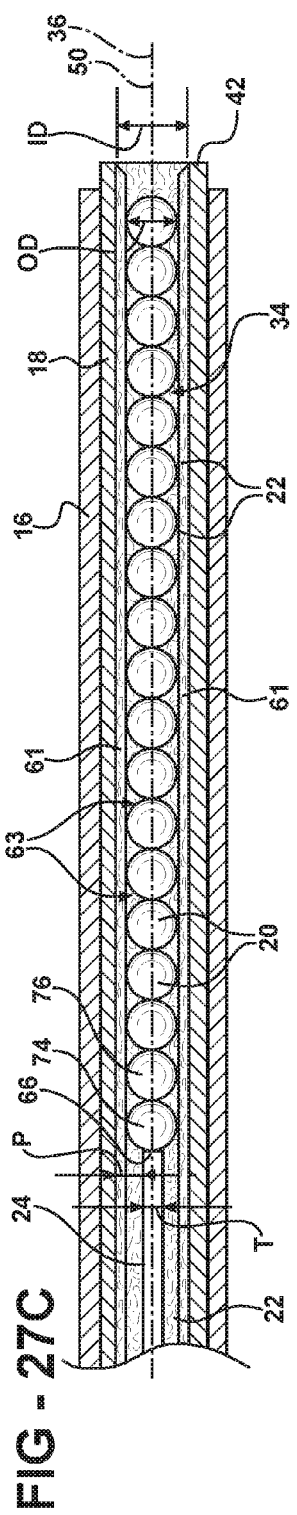

METHOD OF DELIVERING A PLURALITY OF ELEMENTS AND FLUENT MATERIAL INTO A VERTEBRAL BODY

CROSS REFERENCE TO RELATED APPLICATIONS

This application is a divisional of U.S. patent application Ser. No. 11/627,771, filed on Jan. 26, 2007, which is hereby incorporated by reference and claims the benefit of U.S. Provisional Patent Application No. 60/762,779, filed on Jan. 27, 2006, which is hereby incorporated by reference, and U.S. Provisional Patent Application No. 60/808,681, filed on May 26, 2006, which is hereby incorporated by reference.

FIELD OF THE INVENTION

The invention generally relates to a method for delivering elements and a fluent material for implantation into bone.

BACKGROUND OF THE INVENTION

Systems are well known in the art for delivering materials such as bone cement to a target site for medical treatment. One particular use of these types of systems is to treat compression fractures caused by trauma, metastasis, or osteoporosis. A compression fracture occurs when a normal vertebral body of a spine has collapsed or compressed from its original anatomical size. Typically, these vertebrae fail at an anterior cortical wall causing a wedge shaped collapse of the vertebra. Fractures can be painful for the patient typically causing a reduced quality of life. Treatments to repair these fractures are performed to reinforce the fractured bone, alleviate associated pain, and to prevent further vertebral collapse.

One method of treating compression fractures, called balloon assisted vertebroplasty, typically uses fluoroscopy to establish a percutaneous passage in the bone or vertebral body to be treated. This is followed by the insertion of an inflatable balloon-like device into the passage in the vertebral body. Liquids, typically called contrast media, are used to inflate the balloon-like device to compact the cancellous bone about the balloon and/or bone marrow toward the inner cortical wall of the vertebral body, thereby resulting in an enlargement of the passage creating a cavity. The balloon-like device is then deflated and removed from the vertebral cavity, leaving behind a cavity. A biocompatible filling material, such as polymethylmethacrylate (PMMA) bone cement is then delivered while in its flowable form into the cavity. This delivery is performed by using pressure type devices. The filling material is then allowed to set to a hardened condition to provide internal structural support to the bone.

Balloon-like devices require exertion of pressure for expansion of the balloon and/or insertion of flowable materials into the balloon. These balloon-like devices can require high inflation pressures, sometimes as high as 400 psi., in order to obtain the desired cavity size or compaction. These balloon-like devices have been known to fail during inflation due to the high inflation pressures, thin balloon membranes required to fit into the percutaneous passage, and sharp tools or bony structures piercing the membranes. Other mechanical devices have been suggested in order to tamp the bone and create a cavity for subsequent filling with bone cement. In today's art, filling the cavity created by a balloon or tamping device requires applying a pressure to the flowable material. Syringe like devices are typically used to create the pressure to flow the material from a chamber and down a channel into the bone. Once the flowable materials leave the delivery system, they flow toward lower pressure regions through the path of least resistance until the pressure has neutralized with its surroundings. This action occurs in an uncontrollable manner where the user cannot influence the flowable material. In other words, flow of the material and the path that the material takes outside of the delivery system cannot be influenced by the practitioner. These flowable materials have been know to flow along fracture lines, into vascular structure as well as into other cracks, holes or spaces in the bone that may or may not have been known to the practitioner.

Another procedure that relies on delivering bone cement under pressure to treat compression fractures is called vertebroplasty. This method of stabilizing bone follows very much the balloon assisted vertebroplasty procedure described above, except vertebroplasty does not utilize balloons or tools to create a cavity prior to the injection of bone cement. Vertebroplasty is typically performed under fluoroscopic guidance and includes the placement of a cannula into the vertebral body to provide a pathway for the bone cement to enter the vertebral body.

During vertebroplasty, low bone cement viscosity and high injection pressures tend to disperse the bone cement throughout the vertebral body. By utilizing injection pressure, the bone cement takes the path of least resistance, which in some instances can lead to undesirable leaking or extravasations outside of the vertebral body.

It is known in the medical community that instances of leaking outside of the vertebral body occur with the above described procedures. For the most part, these leaks have not caused severe symptoms or complications requiring additional medical intervention. Nevertheless, the following complications have been associated with leaks outside of the vertebral body: epidural hematoma; intrusion into the spinal canal with permanent paralysis, radiculopathy, paresthesias or loss of motor function; pulmonary embolism; pneumothorax; and death.

Another limitation of the current pressure delivery system is the difficulty of visualizing the flowable materials using a fluoroscope. Fluoroscopes are traditionally used by the medical practitioner in order to identify the bony structure, the radiopaque instruments used and the radiopaque flowable materials injected as described above. As mentioned earlier, the practitioner cannot influence the flow of the materials. Once the materials have left the delivery system, these materials can flow through thin cracks or small crevices in a manner where the practitioner cannot see the image of this thin flow on the fluoroscope. As one can appreciate, the inability to see thin flow fronts can mislead the practitioner into applying more pressure to deliver more flowable materials, even when the thin flow fronts are leaking outside the vertebral body and into undesirable locations. An example of a filling material for use in vertebroplasty to overcome these problems can be found in U.S. Pat. No. 6,231,615 to Preissman. Preissman discloses an enhanced visibility composition of a flowable material with radiopaque particles up to 350 (micron) and tracer elements having a size between 570 (micron) and 2200 (micron) for improving the visualization with medical imaging. Preissman, however, did not consider the problem when thin flow fronts exist and the disclosed tracers are separated from the flow when the bony structure restrains the tracers, effectively filtering them, as the flow continues down thin sections.

Recently, in an attempt to overcome these problems, systems have been developed to treat compression fractures by delivering structural elements to distract tissue surfaces forming the collapsed vertebral body. A shortcoming of these systems is the lack of complete stabilization of the bony structure and the lack of a permanent fixation of the implant M to the bone. It is believed that motion of a bony structure of cancellous bone within the vertebral body may result in pain to the patient. Thus, it is desirable to stabilize the cancellous bone to prevent this motion.

U.S. Pat. No. 6,595,998 to Johnson et al. discloses a tissue distraction device for treating compression fractures by inserting a plurality of wafers into a vertebral body to form a wafer stack. Once the wafer stack is formed, the bone cement can be delivered into the vertebral body around the wafer stack to lock the wafers together and form a stable implant M. The wafer stack provides support on upper and lower sides of the vertebral body, but may not provide uniform support on all sides. Also, Johnson et al. does not disclose how much bone cement is delivered and/or whether enough is delivered to stabilize the bony structure of cancellous bone within the vertebral body. Furthermore, this delivery occurs through relatively little control of the flow of pressurized bone cement during delivery, much like as described above.

Another prior art system is described in U.S. Patent Application Publication No. 2005/0278023 to Zwirkoski. In this system, a plurality of segments, flexibly connected to one another, are inserted into a vertebral body to treat a compression fracture. The system includes an applicator having a rotary driver, such as an auger or a cog wheel, for transporting the plurality of flexibly connected segments through a cannula and into the vertebral body. Zwirkoski suggests passage of fluent materials such as bone cement into the vertebral body concurrent with the segments. However, Zwirkoski fails to disclose how to perform this concurrent delivery. Moreover, Zwirkoski does not disclose how much bone cement is delivered and/or whether enough is delivered to stabilize the bony structure of cancellous bone within the vertebral body.

Thus, there is a need in the art for a system that is capable of simultaneously delivering structural elements and fluent material, e.g., delivering a mixture of elements and fluent material, to a vertebral body for medical treatment such that the implant materials are delivered in a controlled manner with a low fluent pressure to reduce leaking. There is also a need for a system that is capable of adjusting relative amounts of elements and fluent material in the mixture delivered to customize a particular procedure based on a patient's anatomy and structural requirements of the final implant M to suitably stabilize the vertebral body. There is also a need to improve the visualization during implantation by increasing the effective radio-opacity of the implant by preventing thin flow fronts.

SUMMARY OF THE INVENTION

The present invention provides a method of delivering a plurality of elements and a fluent material capable of setting into a hardened condition into a vertebral body having an interior of cancellous bone to form an implant. The method comprises placing the fluent material at least partially within a void space defined among the elements in a delivery passage of a delivery cannula. The elements are disposed adjacent to one another in the delivery passage. A push rod is inserted in the delivery passage of the delivery cannula to slide the push rod along the delivery passage and apply a force to a first of the elements and transfer the force through the first element to a second of the elements disposed in the delivery passage to move the elements through the delivery passage and into the interior of the vertebral body such that the fluent material is simultaneously carried with the elements as the elements move through the delivery passage and into the interior of the vertebral body upon application of the force. The fluent material sets to the hardened condition to secure the elements and form the implant. At least one of the delivery cannula, the push rod, and the elements are configured to allow the fluent material to backflow from the void space when inserting the push rod in the delivery passage so that pressurization of the fluent material is reduced.

By delivering the elements under the force of the push rod, the fluent material is transported by the elements and enters into the interior of the vertebral body under a low pressure. This low pressure delivery of the fluent material prevents extravasations which can result from delivering the fluent material under a high pressure. Additionally, amounts of the elements and the fluent material delivered can be highly controlled to ensure adequate stabilization of the bony structure of cancellous bone present within the vertebral body thereby preventing motion of the implant within the vertebral body.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 1 is a partial cross-sectional side view of a system for performing vertebral augmentation with an access cannula and a delivery cannula inserted in an interior of a vertebral body;

FIG. 2 is an exploded cross-sectional side view of the delivery cannula and elements surrounded by a fluent material;

FIG. 3 is a cross-sectional side view of the elements and the fluent material loaded in the delivery cannula;

FIG. 4 is an exploded cross-sectional side view of the delivery cannula, elements, and fluent material of FIG. 3 and the access cannula;

FIG. 5 is an exploded side view of the access cannula, the delivery cannula, and a push rod;

FIGS. 7A-7F are cross-sectional views of the alternative delivery cannulae;

FIGS. 12A-12I are cross-sectional perspective views of delivery cannulae illustrating alternative configurations for the elements;

FIGS. 24A and 24B are cross-sectional side views of a 2-stage system for filling the delivery cannula with elements and the fluent material;

FIG. 25 is a cross-sectional side view of a parallel system for loading the fluent material to the elements as the elements are moved along the delivery passage of the delivery cannula;

FIGS. 26A-26C are cross-sectional top views of the vertebral body illustrating the delivery of the elements and the fluent material to the interior at different volumetric ratios; and FIGS. 27A-27E are cross-sectional side views of the access cannula and delivery cannula of the system exposing the push rod, elements, and fluent material and illustrating the delivery of different volumetric ratios of the elements to the fluent material based on a minimum dimension of the push rod.

DETAILED DESCRIPTION OF THE INVENTION

I. Overview

Figure 6:
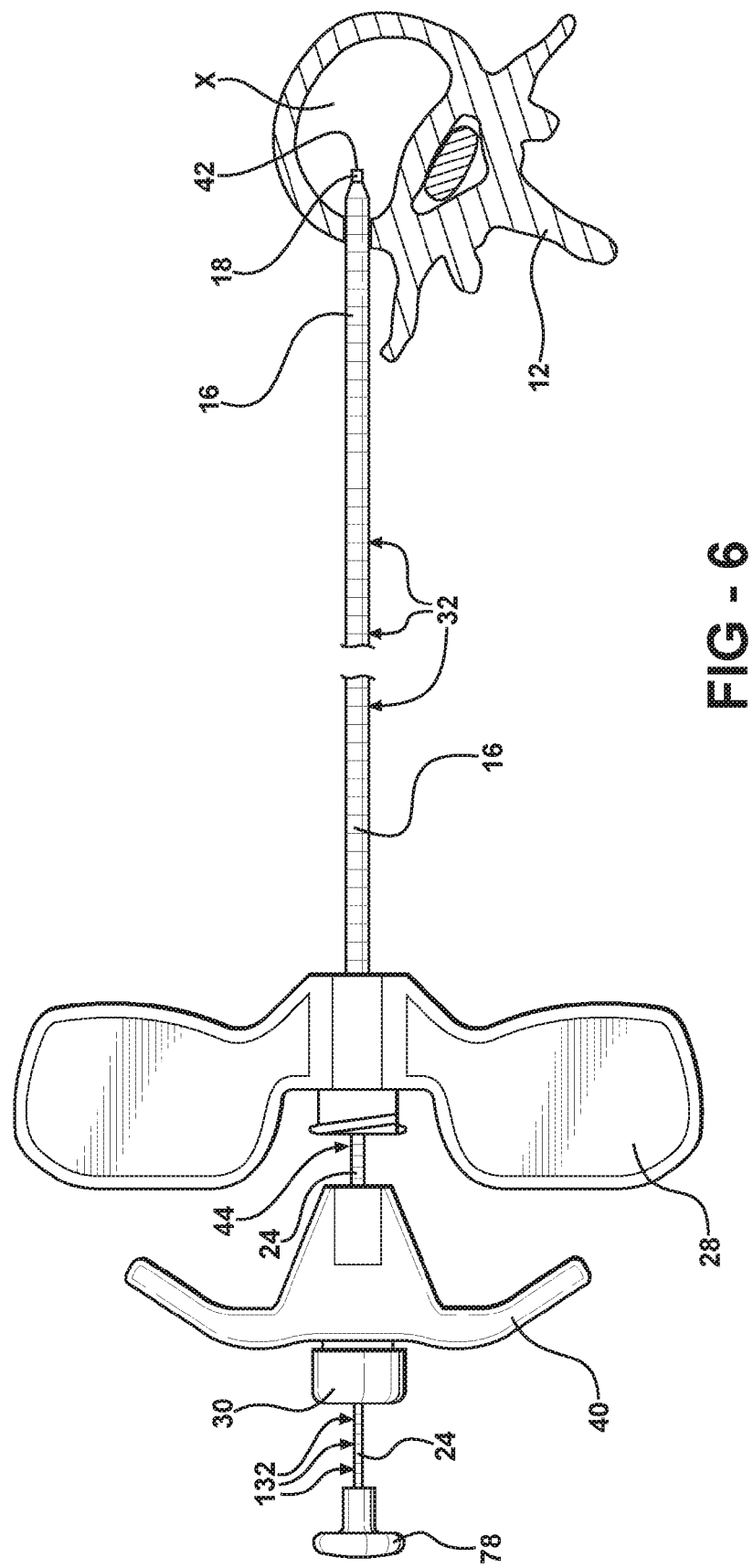
FIG. 6 is a top view of the system showing the access cannula inserted within the vertebral body and the delivery cannula partially inserted within the access cannula and the push rod inserted within the delivery cannula.

Referring to the Figures, wherein like numerals indicate corresponding parts throughout the several views, a system for forming an implant M to stabilize a vertebral body 12 having an interior of cancellous bone 14 is shown generally at 10. The system 10 may be used to treat vertebral compression fractures, for repair of intervertebral discs, as an interbody fusion device, as well as for treating other compression fractures including, but not limited to, tibia plateau fractures, Colles' fractures, crush fractures, or distal tibia fractures. For example, when the vertebral body 12 experiences a compression fracture, the system 10 is used to form an implant M in the interior of cancellous bone 14 of the vertebral body 12 and stabilize the vertebral body 12. The system 10 may also be used for restoring an orbit floor or for elevating soft tissue in cosmetic applications. The system 10 may be used to distract tissue, fill a cavity in tissue (existing or created), reinforce tissue, compress tissue (e.g., cancellous bone), or create a cavity in tissue. Moreover, the system 10 will form the implant M at a low pressure to prevent extravasations of the implant M from the vertebral body 12 thereby preventing the implant M from entering any other part of the body, such as vascular tissue.

II. System Components

Referring generally to FIGS. 1-6, the system 10 includes an access cannula 16, a delivery cannula 18, a plurality of elements 20, a fluent material 22, and a push rod 24. The access cannula 16 is for accessing the interior of the vertebral body 12 and the delivery cannula 18 is sized for insertion in the access cannula 16. The elements 20 and the fluent material 22 are disposed within the delivery cannula 18 where the push rod 24 applies a force on the plurality of elements 20 in the delivery cannula 18 to deliver the elements 20 and the fluent material 22 from the delivery cannula 18 to the interior of the vertebral body 12. Additionally, to facilitate delivery of the elements 20 and the fluent material 22, the system 10 may also include a delivery mechanism 26.

A. Access Cannula

Referring specifically to FIGS. 4-6, the access cannula 16 defines an access passage 29 which is cylindrical for accessing the interior of the vertebral body 12. The delivery cannula 18 is sized for insertion in the access passage 29 of the access cannula 16. The access cannula 16 is preferably formed of a biocompatible material and may be fixed to an access handle 28. The biocompatible material used to form the access cannula 16 may be any biocompatible metal or other material. The access cannula 16 is configured to percutaneously enter a target site X without creating major trauma around the target site X. The access cannula 16 is further configured to accommodate any size, shape, or type of delivery cannula 18, described below. The access handle 28 preferably includes a luer-lock connector 30 for connecting to various instruments for drawing materials from the target site X, delivering materials into the target site X, and the like.

The access handle 28, access cannula 16, or portions of the access cannula 16 may be formed of a radiolucent material for use in a fluoroscopic field. Methods for inserting the access cannula 16 into the tissue to access a target site X are well known in the art and will not be described in detail. For instance, the access cannula 16 may be placed in the vertebral body 12 using a solid stylet (not shown) sized to match the access passage 29. The access cannula 16 may have a threaded distal end (not shown) to secure the access cannula 16 to the tissue, e.g., bone. The access cannula 16 may include markings 32 (see FIG. 5) to approximately determine the depth the access cannula 16 is inserted when inserting the access cannula 16 into the patient to access the target site X. It should be appreciated, however, that the access cannula 16 is not required as the delivery cannula 18 can be used to directly access the interior of the vertebral body 12.

B. Delivery Cannula

Referring specifically to FIGS. 2-6, the delivery cannula 18 defines a delivery passage 34, extending along a delivery axis 36 (see FIG. 2), for providing access to the interior of the vertebral body 12. The delivery passage 34 further defines an exit port 38, open to the delivery passage 34, for allowing the elements 20 and the fluent material 22 to exit the delivery cannula 18 and enter the interior of the vertebral body 12, as illustrated in FIG. 1. The delivery passage 34 has an inner diameter ID for accommodating the push rod 24, which is movably disposed within the delivery passage 34 of the delivery cannula 18.

The delivery cannula 18 is preferably formed of a biocompatible material and is fixed to a delivery handle 40. The biocompatible material used to form the delivery cannula 18 may be any biocompatible metal or other material. The delivery cannula 18 is configured to accommodate any size or shape of the elements 20 being used. In the case of using spherical elements 20, the delivery cannula 18 is preferably in the shape of a cylindrical tube. Of course, any shape may be used for the delivery cannula 18. The delivery handle 40 preferably includes a luer-lock connector 30 for connecting to various instruments for filling the delivery cannula 18 with the fluent material 22, drawing the fluent material 22 from the delivery cannula 18 or target site X, delivering the fluent material 22 into the target site X, and the like.

The delivery handle 40, delivery cannula 18, or portions of the delivery cannula 18 may be formed of a radiolucent material for use in a fluoroscopic field. For instance, in one embodiment, a distal end 42 of the delivery cannula 18 may be radiopaque for determining a position of the distal end 42, while the remaining portion of the delivery cannula 18 is radiolucent to enable viewing of the elements 20 in the delivery cannula 18 during use. The delivery cannula 18 is configured, e.g., sized, for sliding within the access cannula 16. This allows the delivery cannula 18 to be inserted into the access cannula 16 to access the target site X. The delivery cannula 18 may also include markings 32 for determining the depth of insertion of the delivery cannula 18 in the access cannula 16.

Alternative delivery cannulae 18, defining angled delivery openings, are shown in FIGS. 7A-7F. The angled delivery openings facilitate radial and/or axial delivery of the elements 20 and the fluent material 22 to a target site X in the interior of the vertebral body 12. With these angled delivery openings, reaction forces between the delivery cannula 18 and the interior of the vertebral body 12 vary and may require less user applied axial force to position the delivery cannula 18 while ejecting the elements 20 from the delivery cannula 18 into the target site X. This allows the user to better control the location of the delivery cannula 18 while delivering the elements 20 from the delivery cannula 18. Thus, the delivery cannula 18 is less likely to be pushed back out of the target site X, which may happen when the delivery axis 36 extends axially along the central axis 50 of the delivery cannula 18. These delivery cannulae 18 can also be rotated during delivery of the elements 20 to steer or direct the delivery of the elements 20 and the fluent material 22 as desired by the user. When using these angled delivery openings, it is understood that the distal end 42 of the delivery cannula 18 will extend generally beyond a distal end 43 of the access cannula 16 inside the vertebral body 12.

In these embodiments, the exit port 38 opens at a delivery angle 46 of less than 180 degrees to the delivery axis 36 for allowing the elements 20 and the fluent material 22 to exit the delivery cannula 18 at the delivery angle 46 relative to the delivery passage 34. In one embodiment, the elements 20 and the fluent material 22 exits the exit port 38 of the delivery cannula 18 perpendicular to the delivery passage 34. In this embodiment, the delivery angle 46 is about 90 degrees to the delivery axis 36. In other embodiments, the delivery angle 46 may range from about 10 degrees to less than 90 degrees. More preferably, the delivery angle 46 ranges from about 25 degrees to about 65 degrees.

In FIG. 7A, the exit port 38 defines a notch 48 formed in a rounded distal end 42 of the delivery cannula 18 to facilitate delivery of the elements 20 to the target site X in a direction comprising radial and/or axial vectors. In FIG. 7B, one side of the distal end 42 of the delivery cannula 18 is angled inwardly relative to a central axis 50 of the delivery cannula 18 to deflect the elements 20 toward the target site X in a direction comprising radial and/or axial vectors. In FIG. 7C, the distal end 42 of the delivery cannula 18 is beveled such that the exit port 38 facilitates delivery of the elements 20 in a direction comprising radial and/or axial vectors. In FIG. 7D, the delivery cannula 18 has a sharpened, beveled, distal end 42 to penetrate into the tissue at the target site X with a radially oriented exit port 38. The interior surface of the delivery cannula 18 at the distal end 42 is oriented at an acute angle relative to the central axis 50 of the delivery cannula 18 to deflect the elements 20 out through the exit port 38 as they are forced down the delivery cannula 18 by the push rod 24. In this instance, the delivery cannula 18 may be inserted into the target site X with or without the use of the access cannula 16 to deliver the elements 20 into the target site X in a direction comprising radial and/or axial vectors. In FIG. 7E, two openings are provided to deflect the elements 20 in opposite directions to the target site X comprising radial and/or axial vectors.

Alternatively, the delivery cannula 18 may have a sharpened distal end 42 forming a tip 52 for penetrating the tissue at the target site X with a radially oriented exit port 38. As with the embodiment shown in FIG. 7F, the delivery cannula 18 may be inserted into the target site X with or without the use of the access cannula 16 to deliver the elements 20 into the target site X.

Figure 10:
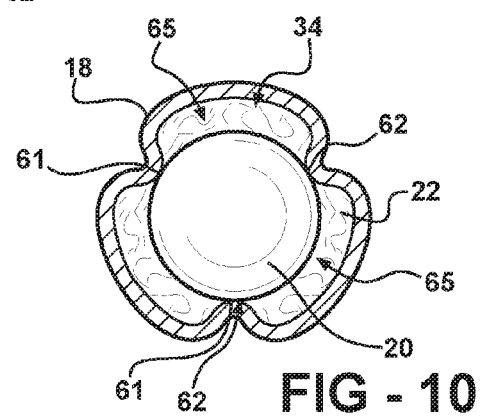
FIG. 10 is a cross-sectional end view of another alternative delivery cannula.

Referring to FIGS. 8A-8C, 9, and 10, further embodiments of the delivery cannula 18 are shown. In these embodiments, the delivery cannula 18 has internal guide ribs 61 for spacing the elements 20 from a delivery wall 62 of the delivery cannula 18. This allows the elements 20 to be held in a linear array, centered on the delivery axis 50. This allows the fluent material 22 to back flow around the elements 20 within the delivery passage 34. The delivery wall 62 surrounds the delivery passage 34 and defines at least one groove 65 open to the delivery passage 34 for holding the fluent material 22. In this embodiment, the grooves 65 are defined between the ribs 61 to allow the fluent material 22 to fill the void spaces 63 between the elements 20 for simultaneous delivery to the target site X. The ribs 61 may be any shape or size with multiple variations to control the alignment of the elements 20 and a volume of fluent material 22 available for delivery to the target site X. The ribs 61 are either part of the delivery wall 62 and define the grooves 65 therebetween, as shown in FIGS. 8A-8C and 9 or the ribs 61 may be a deformed part of the delivery wall 62, as shown in FIG. 10.

Figure 11:
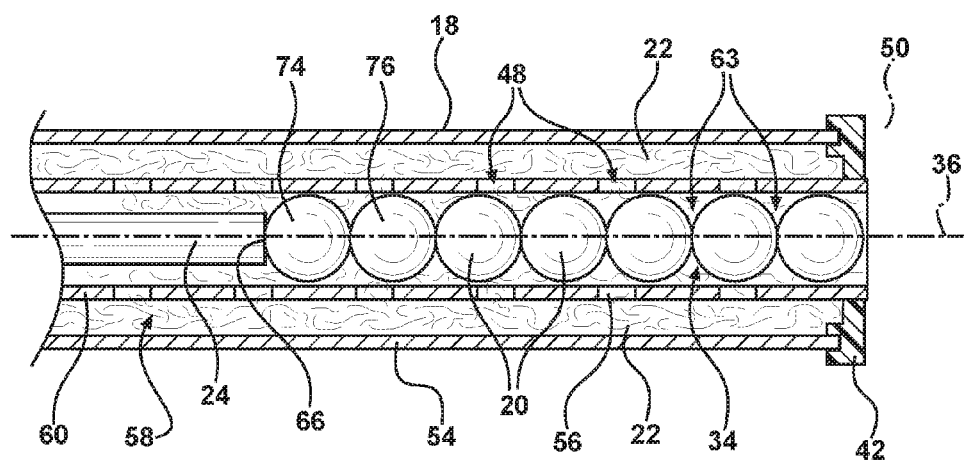
FIG. 11 is a cross-sectional side view of yet another alternative delivery cannulae.
Figure 12F:
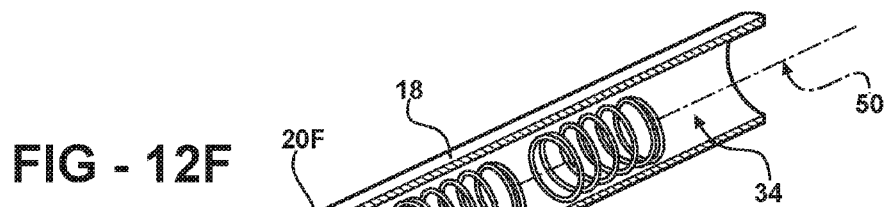
Figure 12G:
Figure 12H:
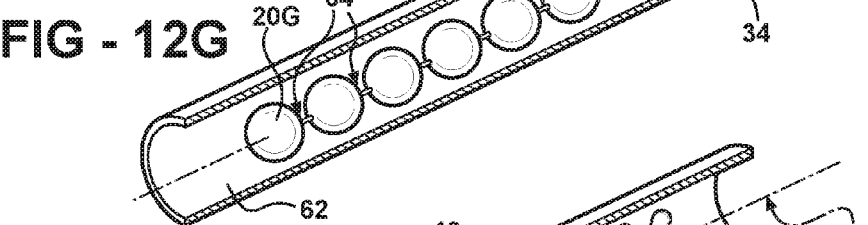
Figure 12I:
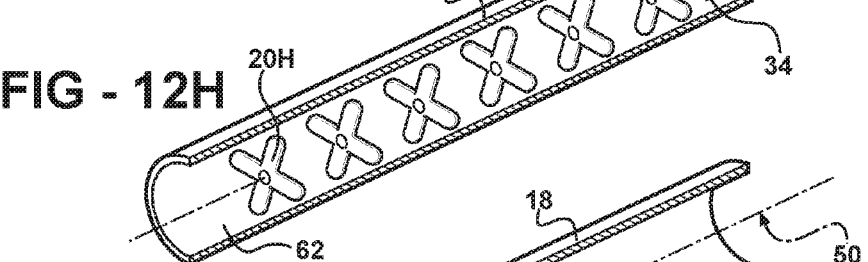
Figure 13:
FIG. 13 is an alternative shape for the element illustrating a whiffle-ball shape defining holes for receiving the fluent material.

FIG. 11 illustrates another alternative delivery cannula 18 of the system 10. The delivery cannula 18 of this alternative embodiment includes an outer sleeve 54 and inner sleeve 56 with an annular space 58 defined therebetween. The elements 20 are loaded into a central lumen 60 defined within the inner sleeve 56, while the fluent material 22 is loaded into the annular space 58 defined between the outer and inner sleeves 54, 56. The inner sleeve 56 is perforated or slotted to allow the fluent material 22 to fill the void spaces 63 between the elements 20 for simultaneous delivery.

C. Elements

The elements 20 preferably have a generally spherical shape and are disposed adjacent to one another in the delivery passage 34 of the delivery cannula 18. The elements 20 are disposed in the delivery passage 34 in a linear array and include at least three elements 20 and at least two void spaces 63 defined between adjacent elements 20 (see FIG. 3). The elements 20 may have an outer diameter OD (see FIG. 8C) substantially equal to the inner diameter ID of the delivery passage 34. However, it should be appreciated that the outer diameter OD of the elements 20 is not limited to being substantially equal to the inner diameter ID of the delivery passage 34 as any outer diameter of the elements 20 may be used to obtain the performance desired by the implant M. The elements 20 may be interconnected by a connecting member 64, which may be flexible. If the elements 20 are interconnected, the connecting member 64 may require severing if the desired volume of the elements 20 and the fluent material 22 has been attained within the interior of the vertebral body 12. To accomplish the severing, the distal end 43 of the access cannula 16 includes a cutter 61 for cutting the connecting member 64 as the access cannula 16 is moved relative to the delivery cannula 18. This means that the access cannula 16 is moved deeper within the interior of the vertebral body 12 to sever the connecting member 64.

Figure 14:
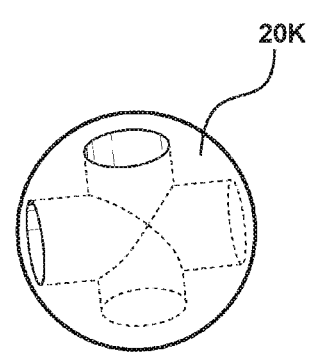
FIG. 14 is yet another alternative shape for the elements illustrating a sphere defining holes for receiving the fluent material.

The elements 20 used with the system 10 may be rigid, semi-rigid, or deformable. The elements 20 can be formed into any shape (pellets, beads, oval-shaped, cylinder-shaped, faceted elements, box-shaped, dumb-bell shaped, nestled shapes, which disconnect upon entering the target site X, coils, etc.). In addition to the spherical elements 20, FIGS. 12A-12I, 13, and 14 illustrate various elements 20 for use with the system 10 of the present invention to form the implant M. Other shapes may include rice shaped elements 20A (FIG. 12A), cylindrically-shaped elements 20B (FIG. 12B), box-shaped elements 20C (FIG. 12C), dumb-bell shaped elements 20D (FIG. 12D), interlocking elements 20E (FIG. 12E), springs 20F (FIG. 12F), interconnected spherical elements 20G (FIG. 12G), cross-shaped elements 20H (FIG. 12H), indented spherical elements 20I (FIG. 12I), whiffle-ball shaped elements 20J (FIG. 13), or semi-hollow spherical elements 20K (FIG. 14).

The number of the elements 20 needed to form the implant M may vary depending on the procedure and the patient. Any combination of element 20 sizes and shapes may be used in the implant M to vary packing characteristics of the elements 20 in the target site X. The elements 20 may also be selected to optimize packing to secure the implant M in the target site X. The size of the elements 20 may be selected to optimize delivery to the target site X and use of the system 10. The elements 20 may also be customized for anatomical considerations, i.e., smaller than cancellous bone 14 pores to build on existing strength in the bone, larger than the cancellous bone 14 pores to displace or compress the bone, sized to plug typical fractures, sized to prevent leaking into vascular tissue, and the like.

The elements 20 may be formed of metals, alloys, ceramics, polymers, bone derived material, or combinations of these materials. Metals that may be used in the elements 20 include, but are not limited to, biocompatible metals and alloys, ferrous or non-ferrous metals, such as stainless steels, gold, silver, tantalum, titanium, platinum, and other alloys, combinations, or equivalents thereof. Polymers that may be used in the elements 20 include, but are not limited to, elastomers, polymethyl methacrylate (PMMA), polyetheretherketone (PEEK), polymethymethacrylate (PMMA), polyvinylchloride (PVC), polyethylene (HDPE, UHMWPE, etc.), polystyrene (PS), polyesters (PET), polyamides (Nylons, aromatic polyamides), polypropylene, fluorocarbon polymers (PTFE, PTFCE, PVF, FEP), and other biocompatible materials.

The elements 20 may be formed of bioabsorbable or non-bioabsorbable material. The elements 20 may also include radiopaque materials to enhance visualization. The elements 20 may also be coated with radiopaque materials. Alternatively, the elements 20 may be formed of radiolucent materials or a combination of radiopaque and radiolucent materials. Additionally, the elements 20 may be coated to provide therapeutic properties. Coatings may include a therapeutic or medicinal material, such as an antibiotic, anticoagulants, biologic agents, radioactive agents (local cancer treatment), bone-growth promoting agents, or combinations thereof. In embodiments employing the connecting member 64, the connecting member 64 may be a wire, string, fiber, or other suitable connector. In other embodiments, loose elements 20 are used, with the elements 20 only being connected together by the fluent material 22 mixed with the elements 20.

D. Fluent Material

The fluent material 22 is preferably capable of setting to a hardened condition and is disposed within at least a portion of the void spaces 63 defined between adjacent elements 20 in the delivery passage 34. The fluent material 22 may be a slurry, liquid, paste, or gel that may solidify during or after delivery. In one embodiment, the fluent material 22 is bone cement, e.g., PMMA bone cement, synthetic bone graft cements, or combinations or substitutions thereof, that solidifies after delivery. The fluent material 22 may also include therapeutic materials, e.g., bone morphogenic proteins, cells or gene therapies, bone growth factors, radioactive agents for local cancer treatment, or combinations or substitutions thereof. In addition, the fluent material 22 may have an affinity to attach to the elements 20, which helps keep the elements 20 associated with one another throughout delivery to form the implant M. The elements 20 may be hollow and/or have perforations and/or passages for the fluent material 22 (see e.g., FIGS. 13 and 14). The elements 20 may have modified surface characteristics, e.g., porous, to better adhere the fluent material 22 to the elements 20 during delivery, to facilitate tissue in-growth, or to reduce overall element 20 weight.

E. Push Rod

Figure 15:
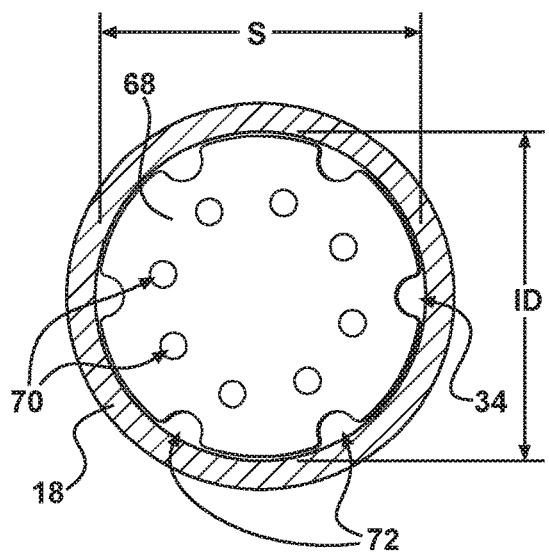
FIG. 15 is a cross-sectional end view of a pusher disposed inside of the delivery cannula.
Figure 16:
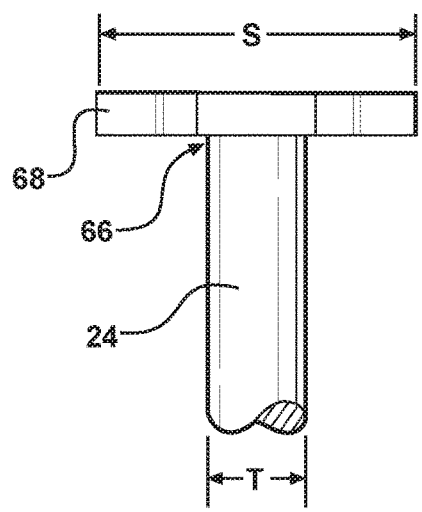
FIG. 16 is a side view of the push rod having the pusher attached.

Referring to FIGS. 5, 15, and 16, the push rod 24 extends to a distal end 66 and has a minimum dimension T. The push rod 24 is shaped and sized for insertion into the delivery cannula 18. In one embodiment, the push rod 24 is a solid metal rod wherein the minimum dimension T corresponds to a diameter that is slightly smaller than the inner diameter ID of the delivery cannula 18 to provide relatively small tolerances between the push rod 24 and the delivery cannula 18. In other embodiments, the push rod 24 and the delivery cannula 18 may define an annular space 58 therebetween for allowing the fluent material 22 to back flow through the annular space 58 as the push rod 24 is moved along the delivery passage 34 of the delivery cannula 18. In this embodiment, the minimum dimension T of the push rod 24, e.g., outer diameter, is less than the inner diameter ID of the delivery cannula 18. As the push rod 24 is moved along the delivery passage 34, this allows the fluent material 22 to backflow around of the elements 20 and into the delivery cannula 18. This further reduces the pressure of the fluent material 22 within the delivery cannula 18. A head 78 (see FIG. 1) can be fixed to the push rod 24 to facilitate gripping and placement of the push rod 24 into the delivery cannula 18.

Referring specifically to FIGS. 15 and 16, the push rod 24 may include a pusher 68 fixed to the distal end 66. The pusher 68 is movably disposed within the delivery passage 34 and has a maximum dimension S for applying the force to the first element 74. The maximum dimension S of the pusher 68 is substantially equal to the inner diameter ID of the delivery passage 34. The pusher 68 and the delivery cannula 18 may define at least one gap 72 therebetween for allowing the fluent material 22 to backflow through the gap 72 as the pusher 68 is moved along the delivery passage 34 of the delivery cannula 18. The pusher 68 may also define a hole 70 for allowing the fluent material 22 to back flow through the hole 70 as the pusher 68 is moved along the delivery passage 34 of the delivery cannula 18. However, it should be appreciated that the invention is not limited to using a pusher 68 as the push rod 24 may be used without the pusher 68.

When the push rod 24 moves along the delivery passage 34, the push rod 24 applies a force to a first element 74, disposed adjacent the push rod 24, and transfers the force through the first element 74 to a second element 76, disposed adjacent the first element 74, and so on down the linear array of elements 20 to move the elements 20 through the delivery passage 34 and into the interior of the vertebral body 12. The elements 20 simultaneously carry the fluent material 22 therewith through the delivery passage 34 and into the interior of the vertebral body 12 upon application of the force to the first element 74. As a result, the elements 20 may compress the cancellous bone 14 within the vertebral body 12 and create interstitial gaps between the elements 20 inside the vertebral body 12. New interstitial gaps can be created between the elements 20 inside the vertebral body 12. These interstitial gaps in the vertebral body 12 correspond somewhat in volume to the previous void spaces 63 present between the elements 20 in the delivery cannula 18. Alternatively, the vertebral body 12 already defines the pre-existing cavity and the cancellous bone does not require compressing. The fluent material 22 is transported by the elements 20 into these interstitial gaps and sets to the hardened condition to lock the elements 20 to one another and form the implant M. As a result, the fluent material 22 is delivered to the interior of the vertebral body 12 at a low pressure which prevents extravasations of the fluent material 22 from the vertebral body 12.

Figure 17:
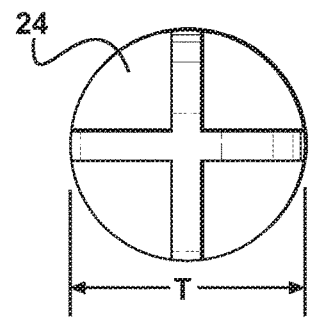
FIG. 17 is a end view of an alternative push rod having a cross shape.
Figure 18:
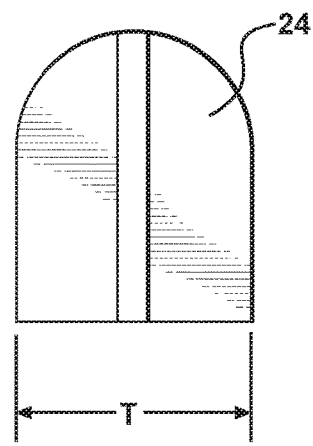
FIG. 18 is a side view of an alternative push rod having a spherical distal end.
Figure 19:
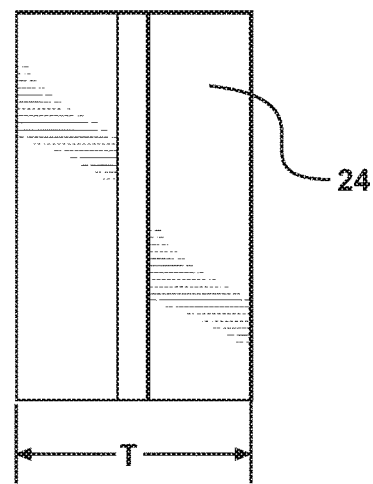
FIG. 19 is a another side view of the alternative push rod having a square distal end.

In other embodiments, shown in FIGS. 17-19, the push rod 24 may have alternative cross-sections, e.g., ribs, or a cross shape, to provide rigidity or stiffness and a tight clearance with the delivery cannula 18, while allowing the backflow of the fluent material 22, e.g., between the ribs and/or allowing the ribs to lie in the grooves 65 in the delivery cannula 18. The distal end 66 of the push rod 24 may be flat, as shown in FIG. 19, spherical, as shown in FIG. 18, or any other shape that is capable of providing the force necessary to deliver the elements 20 from the delivery cannula 18 into the target site X. This push rod 24 has a cross-section which is shaped to work with the delivery cannula 18 shown in FIGS. 8A-8C or FIG. 10. A shaped push rod 24 can be formed to fit inside of these delivery cannulae 18 with portions of the push rod 24 extending radially beyond the guide ribs 61 and into the grooves 65. As is discussed below, this alternate push rod 24 can be used to dispense the implant materials (e.g. elements 20 and fluent material 22) within the guide ribs 61 as well as some or all of the fluent material 22 contained in the grooves 65 of these delivery cannulae 18. This shape of the push rod 24 can provide a way to vary the ratio of the volume of the fluent material 22 relative to the volume of the elements 33 delivered from the delivery cannula 18.

F. Delivery Mechanism

As an alternative to manually pushing the push rod 24, the system 10 may include the delivery mechanism 26 with a force applying mechanism 84. The force applying mechanism 84 may be any mechanism known to those skilled in the art. Suitable mechanisms are shown in U.S. Pat. No. 5,431,654 to Nic and U.S. Patent Application Publication No. 2005/0128867 to Henniges et al., both of which are hereby incorporated by reference. Otherwise, a manual force, e.g., a hand and/or fingers or surgical hammer, is used to press the push rod 24 into the delivery cannula 18, as shown in FIG. 6, to deliver the elements 20 and fluent material 22 from the delivery cannula 18 to the target site X.

Figure 20:
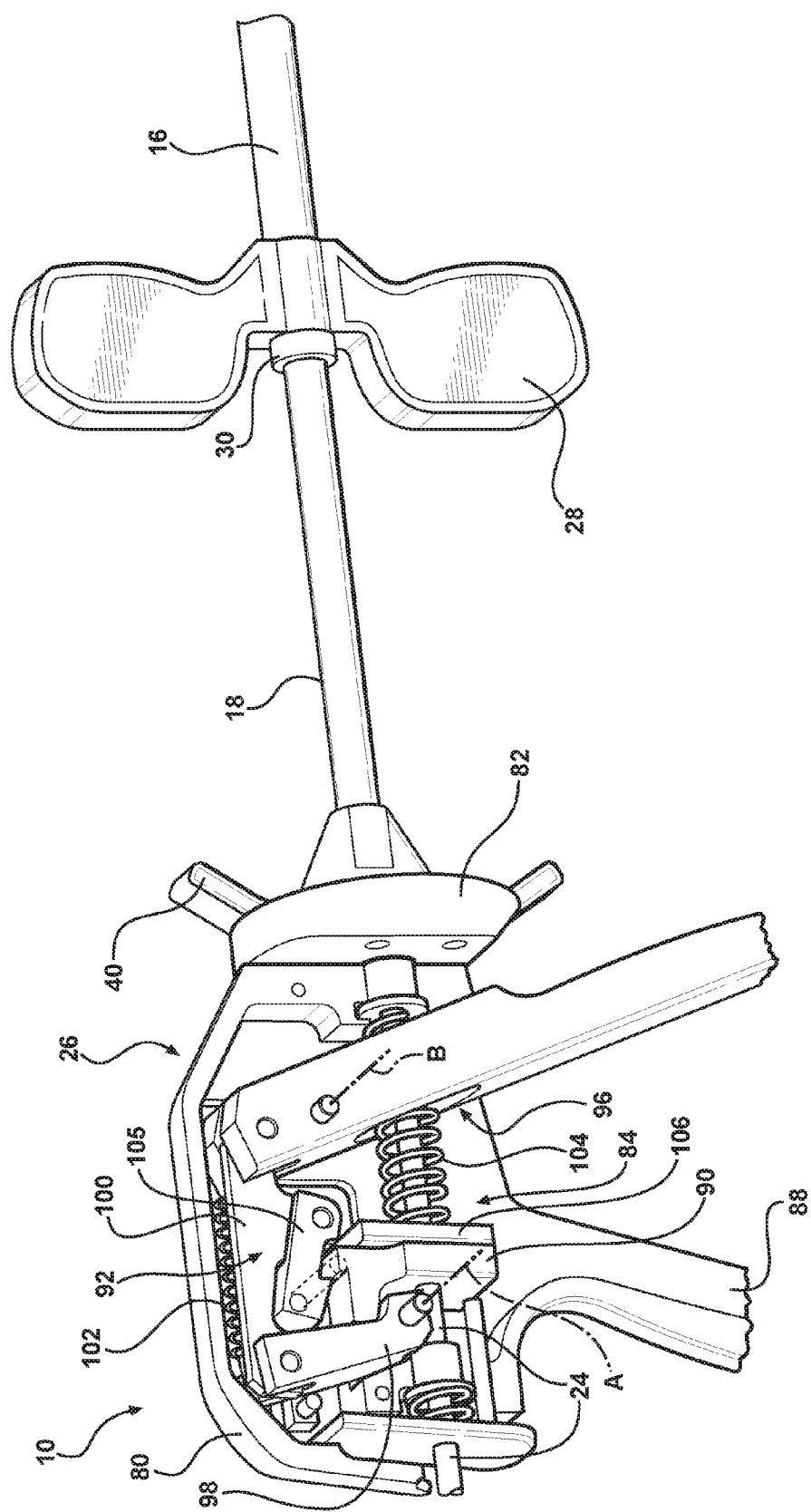
FIG. 20 is a perspective side view of a delivery mechanism having the push rod installed for driving into an attached delivery cannula.

One embodiment of the delivery mechanism 26 is shown in FIG. 20. The delivery mechanism 26 generally includes a housing 80, a connector 82, the force applying mechanism 84, and a trigger 86. A handle 88 is integrally formed with the housing 80 to maneuver the delivery mechanism 26 during use. The connector 82 extends from the housing 80 for engaging the delivery cannula 18.

The force applying mechanism 84 is supported by the housing 80 for applying a force to the push rod 24. The force applying mechanism 84 includes a gripper plate 90 responsive to movement of a linkage system 92 upon actuation of the trigger 86. The gripper plate 90 defines an aperture 96 surrounding the push rod 24. The gripper plate 90 frictionally engages the push rod 24 to advance the push rod 24 along the delivery cannula 18. The gripper plate 90 is urged forward while remaining in frictional contact with the push rod 24 by the linkage system 92 when the trigger 86 is actuated. The gripper plate 90 thereby advances the push rod 24 relative to the housing 80 and the delivery cannula 18 to drive the push rod 24 and force the elements 20 and the associated fluent material 22 from the delivery cannula 18. The trigger 86 is pivotally supported by the housing 80 and operatively connected to the force applying mechanism 84 to advance the force applying mechanism 84 upon actuation of the trigger 86.

The linkage system 92 includes a first link 98, which is pivotally mounted to the housing 80 about a pivot axis A adjacent to the gripper plate 90. The first link 98 is adapted to engage the gripper plate 90 when the first link 98 pivots about the pivot axis A. A second link 100 pivotally interconnects the trigger 86 to the first link 98 via support pins. The links and the trigger 86 are interconnected to move in unison upon rotation of the trigger 86 about a second pivot axis B. When the trigger 86 is pulled, the second link 100 rotates the first link 98 about the pivot axis A, which engages the gripper plate 90 and urges the gripper plate 90 forward while the gripper plate 90 remains in frictional engagement with the push rod 24 thereby advancing the push rod 24. A return spring 102 returns the links and the trigger 86 to an initial position upon release of the trigger 86. At the same time, a first spring 104 momentarily disengages the gripper plate 90 from the push rod 24 to slide the gripper plate 90 back to an initial position to await the next pull of the trigger 86. The housing 80 pivotally supports the first link 98 and the trigger 86 about the pivot axes A and B via support pins.

A release pin 105 disengages the gripper plate 90 to allow a user to freely move the push rod 24 by hand. The release pin 105 is connected to a retainer plate 106 and is adapted to engage the gripper plate 90. When the retainer plate 106 is pushed by the user, the release pin 105 engages the gripper plate 90 which forces the gripper plate 90 to tilt back against the bias of the first spring 104 thus releasing the push rod 24. As should be appreciated, pushing the retainer plate 106 also pivots the retainer plate 106, releasing its engagement with the push rod 24. With both the retainer plate 106 and the gripper plate 90 released, the push rod 24 is free to move. This allows the user to manually move the push rod 24 with respect to the housing 80.

The delivery mechanism 26 is adapted to engage the push rod 24 and the delivery cannula 18 and provides the force of the push rod 24 while holding the delivery cannula 18 to allow relative movement between the push rod 24 and the delivery cannula 18. This means that the delivery cannula 18 is mounted to the delivery mechanism 26, by the connector 82, and the push rod 24 is coupled with the force applying mechanism 84. This relative movement between the push rod 24 and the delivery cannula 18 moves the elements 20 and the fluent material 22 along the delivery passage 34 and into the interior of the vertebral body 12.

Figure 21:
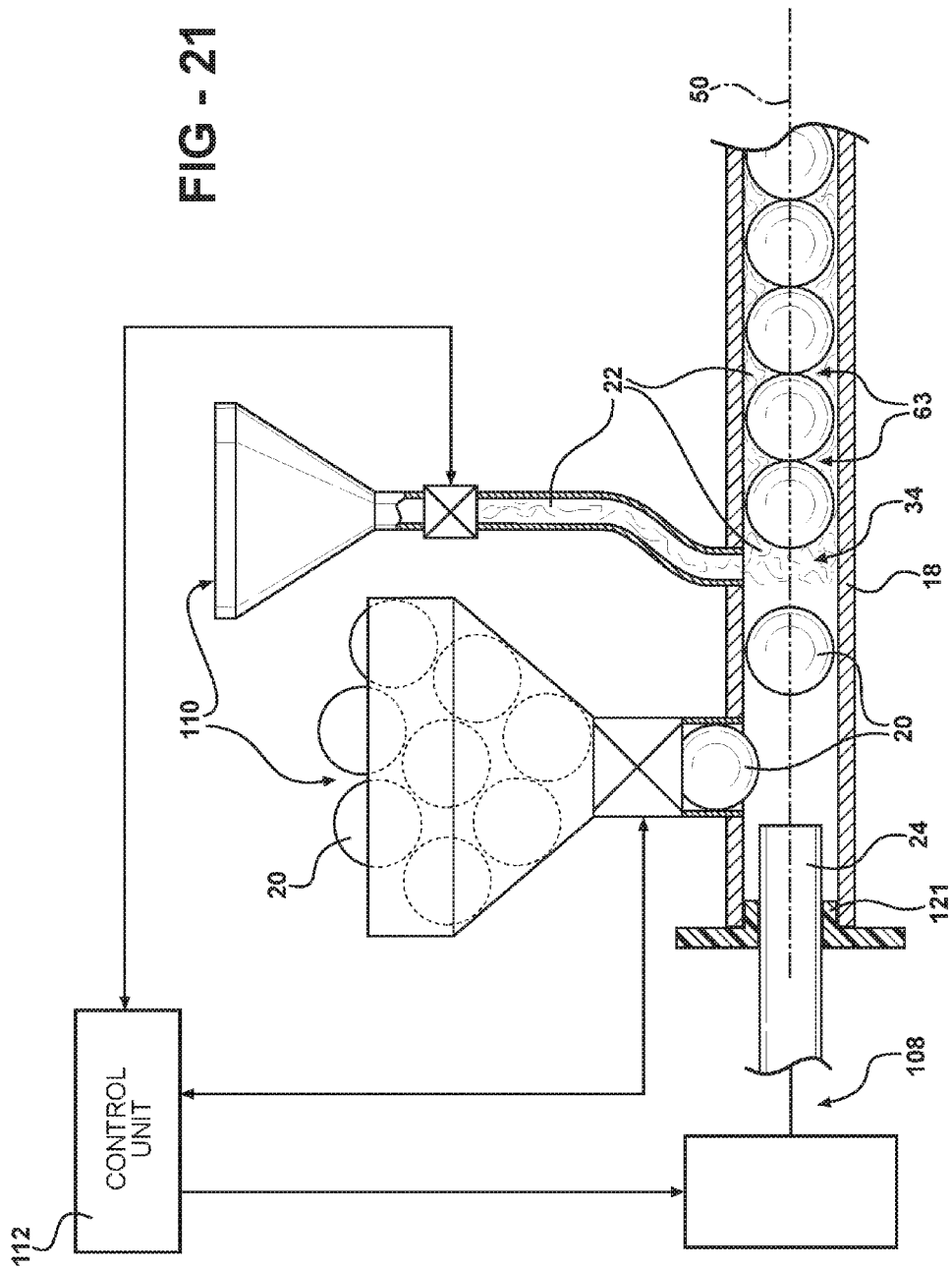
FIG. 21 is a another embodiment for filling the delivery passage of the delivery cannula with the elements and the fluent material.

Referring to FIG. 21, in an alternative system 10 of the present invention, the force used to deliver the elements 20 and the fluent material 22 can be replaced by an automatic system comprising a reciprocating driver 108 with the push rod 24 used with a modified delivery cannula 18. In this embodiment, the elements 20 and the fluent material 22 are stored within hoppers 110 or other suitable containers 124 for feeding to metering units that can be set by a controller 112 to adjust the relative amounts of the elements 20 and the fluent material 22 dispensed from the hoppers 110 into the delivery cannula 18 for delivery to the target site X. The reciprocating driver 108 is controlled by the controller 112, as set by the user, to customize delivery of the elements 20 and the fluent material 22 to the target site X to form the final implant M. This system 10 may be set to deliver a fixed or variable volume of the fluent material 22 based on a fixed or variable volume of the elements 20 dispensed into the delivery cannula 18.

G. Kits

Figure 22:
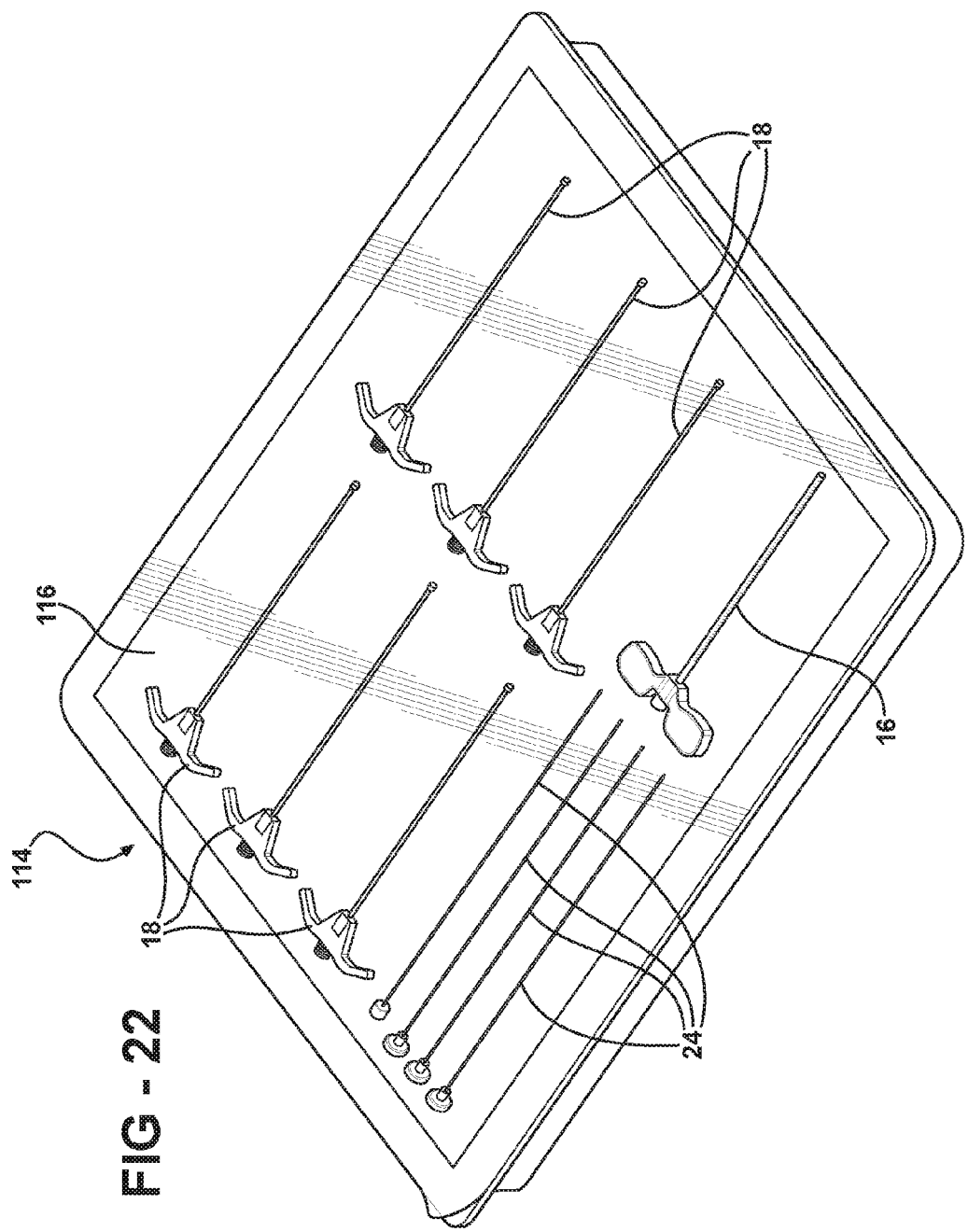
FIG. 22 is a kit for the system.
Figure 23:
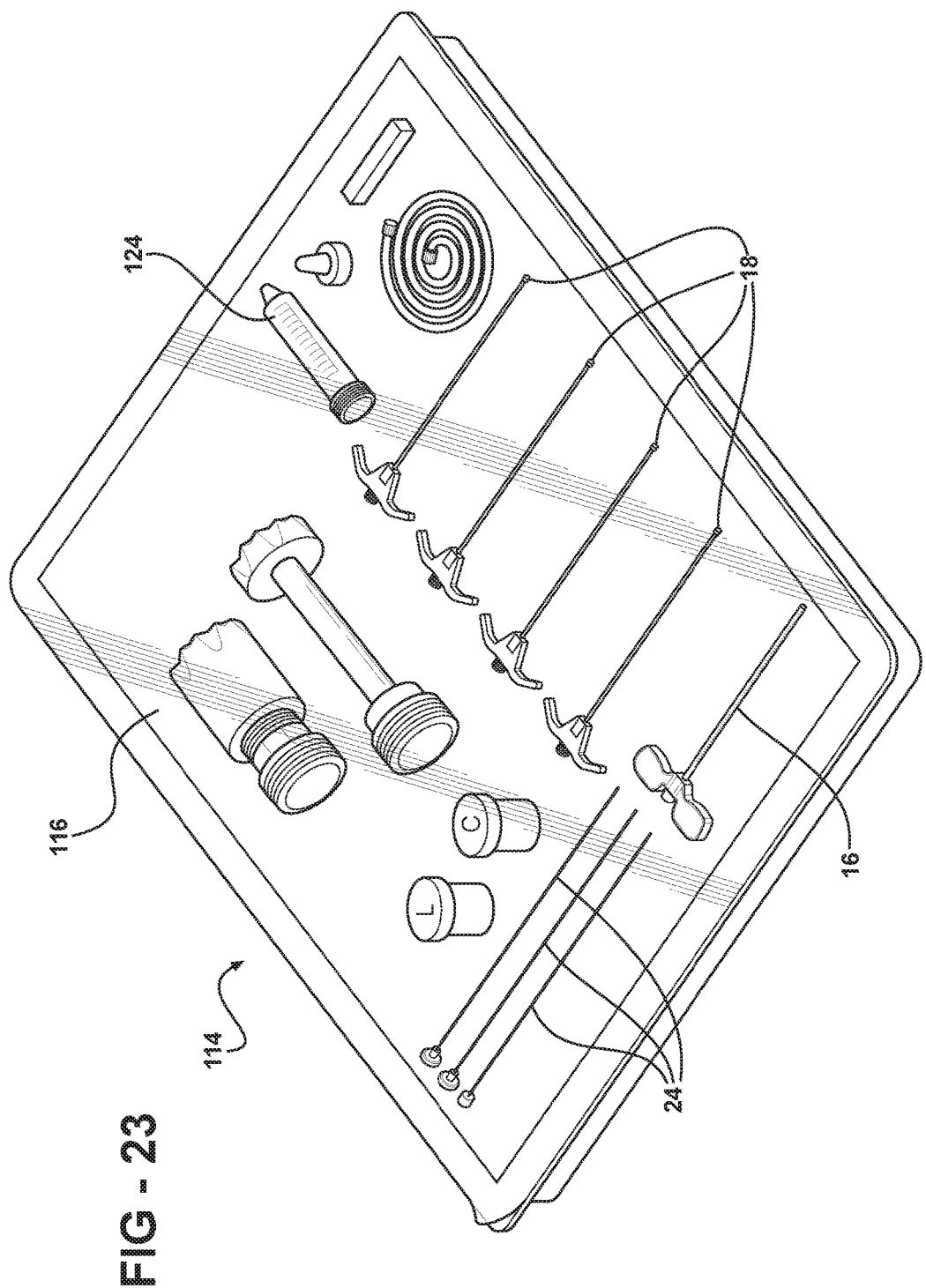
FIG. 23 is an alternative kit for the system.

Referring to FIGS. 22 and 23, various kits 114 may be provided with selected components of the system 10. In one exemplary kit, a sealed tray 116 or other type of package may include the access cannula 16, delivery cannula 18, and push rod 24, with the delivery cannula 18 being pre-loaded with the elements 20 and sealed with end caps 118, 120. Optionally, the delivery cannula 18 is pre-loaded with the fluent material 22, when the fluent material 22 is of a type that does not set in storage. A stylet (not shown) or other suitable device, used with or without a guide wire, may also be provided in the kit 114 for introducing the access cannula 16 into the target site X. As shown in FIG. 23, a bone cement delivery device may also be provided in the kit 114 for filling the delivery cannula 18 with the fluent material 22 in the void spaces 63 between the elements 20, such as a PCD® Precision System available from Stryker Instruments of Kalamazoo, Mich. The kit 114 may further include a liquid monomer L and powdered copolymer C for mixing together to form the fluent material 22 to be loaded into the delivery cannula 18 prior to use. Each of the kits 114 may be sterilized using techniques known to those skilled in the art. The delivery mechanism 26 may or may not be provided with this kit 114 depending on the particular needs of the user.

III. System Operation

A. Loading the Elements and the Fluent Material into the Delivery Cannula

The delivery cannula 18 may be preloaded with the elements 20 during shipping to facilitate use. In this instance, the distal end cap 118 is fitted onto the distal end 42 of the delivery cannula 18 and the proximal end cap 120 is luer-locked onto the luer-lock connector 30 mounted on the delivery handle 40. These end caps 118, 120 or other containment members can be used to hold the elements 20 in the delivery cannula 18 between a proximal end and the distal end 42. The end caps 118, 120 may have vents 119 to allow air to pass while filling the fluent material 22 into the delivery cannula 18. The proximal end cap 120 may include a seal 121, e.g., wiper, which allows insertion of the push rod 24 into the proximal end cap 120, while securing the elements 20 in the delivery cannula 18. The seal 121 may also retain the fluent material 22 within the delivery cannula if a viscosity of the fluent material 22 is low and/or to manage the pressure of the fluent material 22. The distal end cap 118 is removed prior to delivery of the elements 20 and fluent material 22 to the target site X.

Loading the elements 20 and the fluent material 22 can be facilitated by the geometry or configuration of the delivery passage 34 of the delivery cannula 18. As discussed above, the delivery passage 34 of the delivery cannula 18 may define grooves 65 and have ribs 61 for allowing the fluent material 22 to flow around the elements 20. This can provide better coverage of the elements 20 and/or improve the filling of the delivery cannula 18 with the fluent material 22.

Figure 24A:
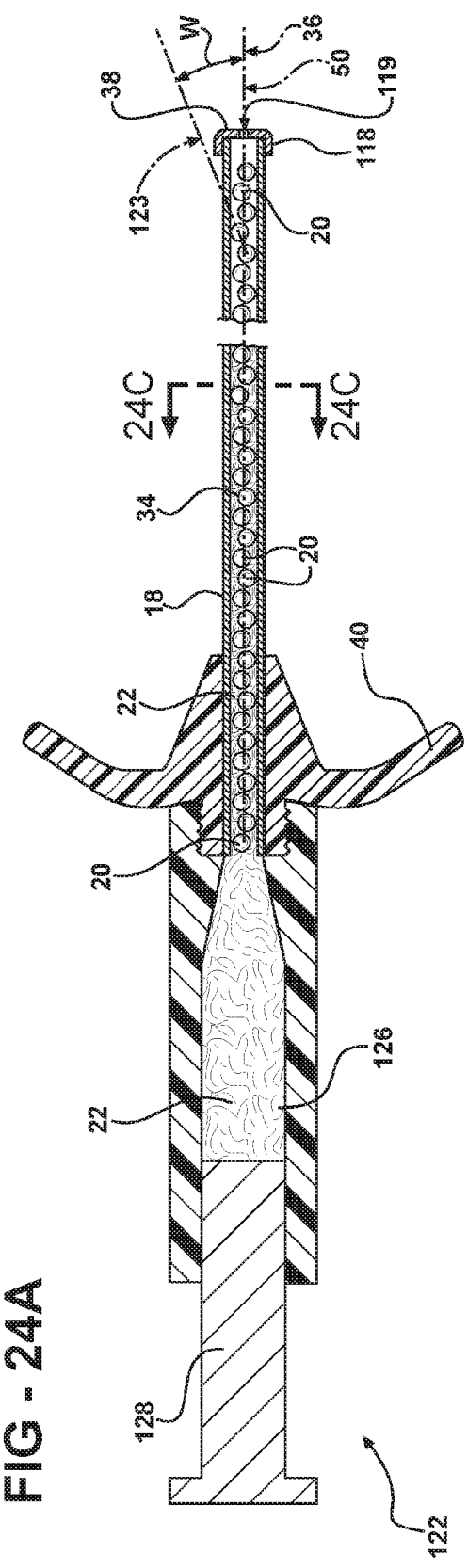
Figure 24C:
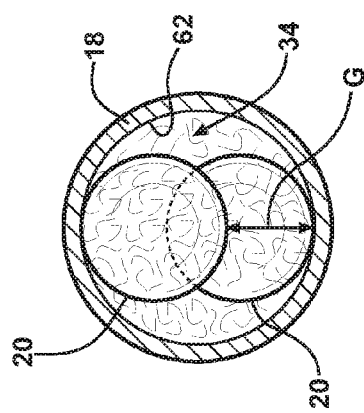
FIG. 24C is a cross-sectional end view taken along line 24C-24C of FIG. 24A.

Referring to FIGS. 24A and 24C, loading the elements 20 and the fluent material 22 can also be facilitated by placing the elements 20 in a staggered configuration in the delivery passage 34 such that gaps G are defined between the elements 20 and the delivery cannula 18, as shown in FIG. 24C. A 2-stage fill system 122 may be used to fill the delivery cannula 18 with the fluent material. The fill system 122 includes a container 124, defining a loading chamber 126, and a mover 128 for inserting into the loading chamber 126. In one embodiment, the fill system is a conventional syringe with plunger. The fluent material 22 is disposed in the loading chamber 126 of the container 124. The mover 128 is then inserted in the loading chamber 126 and the container 124 is coupled to the delivery cannula 18. The mover 128 is manually or mechanically pressed to force the fluent material 22 from the loading chamber 126 into the delivery passage 34 of the delivery cannula 18. The fluent material 22 flows around the elements 20 in the delivery passage 34 to at least partially fill the void spaces 63 by flowing or moving through the gaps G and into the void spaces 63. Furthermore, because the elements 20 are staggered within the delivery passage 34, adjacent elements 20 align along a wedge axis 123 with a wedge angle W defined between the wedge axis 123 and the central axis 50. After the delivery cannula 18 is loaded with the elements 20 and the fluent material 22, as the force is applied to the elements 20 by the push rod 24, the force is transferred through the adjacent elements 20 along the respective wedge axes 123. This may result in an increase in the overall force which is required to move the elements 20 and the fluent material 22 from the delivery cannula 18 and into the target site X.

Referring to FIG. 24B, as an alternative, the elements 20 and the fluent material 22 are loaded into the delivery cannula 18 using the 2-stage fill system 122 where the elements 20 and fluent material 22 are disposed in the loading chamber 126 of the container 124. Preferably, the container 124 is sized accommodate the elements 20 and sufficient spacing between and around the elements 20 such that the fluent material 22 easily flows through the elements 20 to fill spaces between the elements 20 and to surround the elements 20. The mover 128 is then inserted in the loading chamber 126 and the container 124 is coupled to the delivery cannula 18. The mover 128 is manually or mechanically pressed to force the elements 20 and the fluent material 22 from the loading chamber 126 into the delivery passage 34 of the delivery cannula 18. As a result, the elements 20 and fluent material 22 are now loaded into the delivery cannula 18 and define the void spaces 63 between adjacent elements 20 with the fluent material 22 at least partially filling the void spaces 63 in the delivery passage 34. This allows the elements 20 to be placed in a tight fitting linear array within the delivery passage 34 while still allowing the fluent material 22 to be sufficiently filled in the void spaces 63 between the elements 20. By aligning the elements 20 more linearly, the wedging of the elements 20 during delivery is reduced. As the wedging angle W increases, more friction builds between elements 20 and the delivery cannula 18.

Referring to FIG. 25, as another alternative, a parallel system 130 simultaneously delivers the elements 20 and the fluent material 22 to the interior of the vertebral body 12. The elements 20 and the fluent material 22 are preloaded into the delivery cannula 18 in separate delivery passages 34A, 34B. An alternative push rod 24A is inserted in the delivery passage 34 of the delivery cannula 18. The push rod 24A consists of two interconnected push rod portions 24B, 24C, extending in tandem. Each of the push rod portions 24B, 24C applies an equal force on the respective fluent material 22 and the elements 20. Alternatively, two independent push rods (not shown) may be used. The push rod portion 24C is moved along the delivery passage 34B to apply the force to the elements 20 to move the elements 20 through the delivery passage 34 and into the interior of the vertebral body 12. At the same time, the push rod portion 24B is moved along the delivery passage 34A to apply the force to the fluent material 22 to move the fluent material 22 into the delivery passage 34B and into the void spaces 63 between the elements 20. As a result, the fluent material 22 is introduced within at least a portion of the void spaces 63 in the delivery cannula 18 as the elements 20 move through the delivery passage 34, but before the elements 20 exit the delivery cannula 18 and enter the interior of the vertebral body 12. This allows the elements 20 and the fluent material 22 to be loaded into the parallel system 130 into separate delivery passages 34A, 34B while still allowing the elements 20 and the fluent material 22 to be delivered to the interior of the vertebral body 12 simultaneously.

Figure 8A:
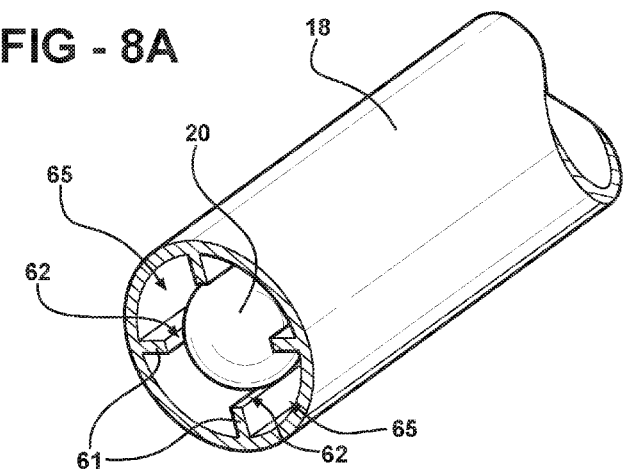
FIG. 8A is a cross-sectional perspective view of another alternative delivery cannulae.
Figure 8B:
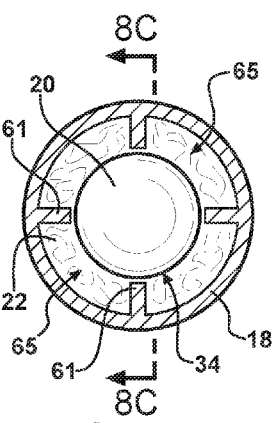
FIG. 8B is a cross-sectional end view of the delivery cannula of FIG. 8A.
Figure 8C:
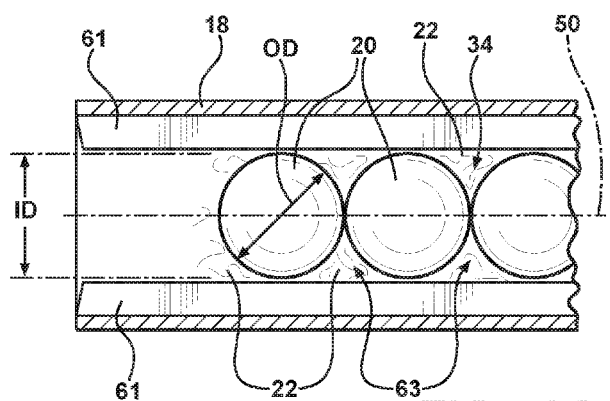
FIG. 8C is a cross-sectional side view of the delivery cannula of FIG. 8A.
Figure 9:
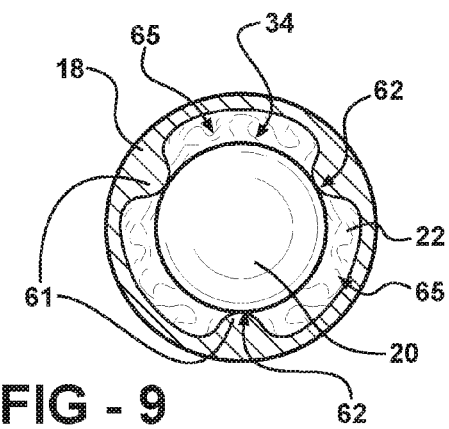
FIG. 9 is a cross-sectional end view of an alternative delivery cannula.

When working with fluent materials 22 which are relatively viscous, such as mixed bone cement, it can be difficult to load the fluent material 22 into the void spaces 63 between the elements 20 when the gap G defined between the elements 20 and the delivery cannula 18 is small. An alternate method of loading the fluent material 22 into the void spaces 63 between the elements 20, but prior to delivery into the target site X is a 3-stage delivery system. A loading cannula with a cross-section as shown in FIGS. 8A-8C or FIG. 10, or a similar cross-section, can be loaded with appropriate sized elements 20, for example, spherical elements 20 with an outer diameter OD which fits within the inner diameter ID of the guide ribs 61, as shown in FIGS. 8A-8C. This loading cannula can then be connected to a fluent material source, such as a syringe-like device. The syringe can be used to create a pressure on the fluent material 22 so that the fluent material 22 flows down a passage in the loading cannula to exhaust the air from the passage of the loading cannula, filling the void spaces 63 between the elements 20. This loading cannula can then be connected to an empty delivery cannula 18. For example, a cylindrical delivery cannula 18 with an inner diameter ID that fits snugly to the outer diameter OD of the elements. A loading push rod can be inserted into the loading cannula and used to transfer the elements 20 and a portion of the fluent material 22 (e.g. fluent material 22 residing in the void spaces 63 defined between the elements 20). The transfer can occur through the application of a force on the first element 74 where that force acts through all subsequent adjacent elements 20 in order to move the mixture into the delivery cannula 18. The loading cannula and loading push rod can then be removed and a push rod 24 can be inserted into the delivery cannula 18 to deliver the implant mixture 20, 22 to the target site X as earlier described.

One advantage in this alternate loading method is when a delivery cannula 18 needs to fit into a smaller access cannula 16 or a smaller delivery cannula 18 is needed to fit into a limited anatomical bone space, the delivery cannula 18 described above would not be burdened with the additional radial size needed to load the relatively viscous fluent material 22. In other words, a delivery cannula 18 with a smaller diameter containing a mixture of fluent material 22 and elements 20 can be made available when needed. Another advantage of this 3-stage loading method is that when the elements 20 are constructed of a material which needs a larger surface area to support and align the elements 20 to be successfully delivered without lodging or wedging the elements 20 in the delivery cannula 18, a delivery cannula 18 without ribs 61 can be used. The delivery cannula 18 without ribs 61 would have a larger surface area to support and align the elements 20 as compared to a similarly sized delivery cannula 18 with ribs 61. This may allow the elements 20 to be delivered to the target site X and overcome resistance of the bone or tissue at the target site X, which may require a higher delivery force to dispense the implant mixture 20, 22.

B. Disposing the Elements and the Fluent Material into the Vertebral Body

The elements 20 and the fluent material 22 are disposed in the interior of the vertebral body 12 by first inserting the access cannula 16 into the vertebral body 12 to provide access to the interior of the vertebral body 12. However, as noted above, the access cannula 16 is not required as the delivery cannula 18 may provide access to the interior of the vertebral body 12. Several known methods could be used to place the access cannula 16 in position. Once such method includes using a stylet (not shown) inserted into the access cannula 16 to penetrate the tissue. Once in position, the stylet is removed from the access cannula 16, leaving the access cannula 16 in place.

Once the access cannula 16 is in place, the delivery cannula 18 is inserted through the access passage 29 in the access cannula 16 and into the interior of the vertebral body 12, as shown in FIG. 6. If used, the delivery mechanism 26 is attached to the push rod 24 and the delivery cannula 18, as shown in FIG. 1. The delivery mechanism 26 is attached to the delivery cannula 18 to hold the delivery cannula 18 relative to the push rod 24. The push rod 24 will apply the force on the elements 20 that are disposed in the delivery passage 34. When the delivery mechanism 26 is attached to the delivery cannula 18, the elements 20 and/or the fluent material 22 may already be loaded in the delivery passage 34 using, for example, the 2-stage fill system 122 discussed above. This depends on the type of loading system being employed. The trigger 86 mechanism of the delivery mechanism 26 is then actuated to move the push rod 24 along the delivery passage 34 of the delivery cannula 18 to apply the force on the elements 20 disposed in the delivery passage 34 of the delivery cannula 18.

As the elements 20 are forced from the delivery cannula 18 via the force applied by the push rod 24, the elements 20 are forced into the interior of the vertebral body 12 at a low pressure (discussed in more detail below). Additionally, the elements 20 simultaneously carry the fluent material 22 through the delivery passage 34 and into the interior of the vertebral body 12 upon application of the force to the elements 20 by the push rod 24. As a result, the elements 20 may compress the cancellous bone 14 within the vertebral body 12 and the fluent material 22 sets to a hardened condition to lock the elements 20 to one another and form the implant M. The fluent material 22 may also interdigitate with the cancellous bone 14 to further provide strength to the vertebral body 12.

During the procedure, the user may gauge the volume of the fluent material 22 delivered to the interior of the vertebral body 12 by measuring a linear distance the push rod 24 travels along the delivery passage 34 of the delivery cannula 18. From the linear distance, the volume of the elements 20 and the fluent material 22 can be calculated or estimated. This allows the user to better understand the volume of the elements 20 and the fluent material 22 already delivered and to estimate the volume of the elements 20 and the fluent material 22 still to be delivered to the interior of the vertebral body 12. Alternatively, the push rod 24 may include a gauge 132, such as markings along the push rod 24, indicating the volume of the fluent material 22 and the elements 20 delivered or the volume of the fluent material 22 and the elements 20 remaining in the delivery passage 34.

The user may perform the procedure using a fluoroscope (not shown). When using the fluoroscope, the elements 20 and/or the fluent material 22 are preferably radiopaque. This allows the user to gauge not only the volume of the elements 20 and the fluent material 22 delivered, but also to assess where the elements 20 and the fluent material 22 are entering and filling the interior of the vertebral body 12.

As an alternative, sensors (not shown) may be used for registering implant M, element, and system, parameters. In one embodiment, the system 10 includes a sensor or transducer for indicating the force applied to the elements 20 and/or the pressure applied to the fluent material 22 during delivery of the elements 20 and the fluent material 22 to the target site X. Closed loop feedback mechanisms may also be used to regulate the actions of the system 10, based on detector readings. For instance, such sensors may be used with the automatic system shown in FIG. 21 to provide closed loop feedback control of the system 10 based on force, pressure, or other parameters. Sensors may also be used to indicate the construct of the implant M. For example, a sensor may indicate the volume of the elements 20 delivered to the target site X, the volume of the elements 20 left in the delivery cannula 18, and/or the position of the implant M within the target site X. In one embodiment, the push rod 24 includes a force gauge (not shown) to detect a force applied by the push rod 24 on the elements 20 and the fluent material 22 being delivered.

The system 10 may also include a display capable of indicating any status measured by such sensors. Examples of the information that the display could indicate includes, but is not limited to, force applied, total volume, linear feed rate, volume feed rate, volume of elements 20 and/or fluent material 22 inserted, and/or volume of elements 20 and/or fluent material 22 remaining in the delivery cannula 18.

C. Delivery of the Elements and the Fluent Material at Low Pressure

1. Forces and Pressure within the System, Generally

As the elements 20 are delivered to the target site X in the vertebral body 12, reaction forces transfer through the system 10 back to the user. The user manually controls and reacts to the reaction forces by delivering the elements 20 under the force to deform or displace the tissue, e.g., bone, at the target site X, to construct the implant M. The reaction forces are transferred as follows: (1) tissue resistance force, (2) elements 20 force, (3) push rod 24 force, and (4) driver force and/or manual force. The elements 20, when delivered to the target site X, define the interstitial gaps between the elements 20 inside the vertebral body 12. The fluent material 22 is transported by the elements 20 into these interstitial gaps and preferably sets to the hardened condition to lock the elements 20 to one another and form the implant M. Since the void spaces 63 defined between the elements 20 in the delivery cannula 18 correspond somewhat to the interstitial gaps between the elements 20 in the final implant M, pressure of the fluent material 22 can be controlled. As a result, the fluent material 22 can be delivered to the interior of the vertebral body 12 at a low pressure which prevents extravasations of the fluent material 22 from the vertebral body 12.

2. Pressure Control

Pressure in the system 10 can be controlled and/or modified by varying a volumetric ratio of the elements 20 to the fluent material 22. Consider the following three examples.

EXAMPLE 1

If the volume of the fluent material 22 delivered from the delivery cannula 18 is equal to the final volume available for the fluent material 22 in the interstitial gaps provided by the elements 20 in the final implant M, then fluent material 22 does not have to be delivered by displacement (pressure), but is transported or carried solely by the elements 20. Therefore, the fluent material 22 experiences no pressurization in the final implant M. In this instance, the likelihood of the fluent material 22 leaking outside of the implant M is reduced. This condition is illustrated in FIG. 26A. This is advantageous for percutaneous treatment of vertebral compression fractures since the likelihood of fluent material 22 leaking from the vertebral body 12 due to pressurization in the fluent material 22 would be minimized.

EXAMPLE 2

If the volume of the fluent material 22 delivered from the delivery cannula 18 is greater than the final volume available for the fluent material 22 in the interstitial gaps provided by the elements 20 in the final implant M, then at least a portion of the fluent material 22, i.e., the volume of the fluent material 22 equal to the volume difference, must be delivered by displacement and/or transported by the elements 20. Therefore, the fluent material 22 experiences a positive pressure and it would be expected that this pressure in the fluent material 22 will attempt to move until it finds a state of equilibrium within its surroundings at the target site X. As illustrated in FIG. 26B, when there is a positive pressure on the fluent material 22 the fluent material 22 moves to an outer boundary or periphery of the implant M. In some cases, it may be desirable to provide some of the fluent material 22 at the outer boundary of the implant M to better secure the implant M in the target site X, to bond with cancellous bone 14 outside of the implant M, and the like. Therefore, some pressure in the fluent material 22 may be advantageous if controlled, such as by the system 10 of the present invention. It should be noted that the volume of the fluent material 22 delivered in excess of the interstitial spaces between the elements 20 is a small percent of the total volume delivered. Therefore, it is expected that the fluent material 22 finds a state of equilibrium by displacing only a small volume of bodily fluids present in the vertebral body 12. This reduces the chances of extravasation.

EXAMPLE 3

If the volume of the fluent material 22 delivered from the delivery cannula 18 is less than the final volume available for the fluent material 22 in the interstitial gaps provided by the elements 20 in the final implant M, then the fluent material 22 does not have to be delivered by displacement, but may be transported solely by the elements 20. Therefore, the fluent material 22 experiences a theoretical negative pressure and not all of the interstitial spaces between the elements 20 in the target site X are filled with the fluent material 22, as illustrated in FIG. 26C. It may be desirable to provide an implant M that is loosely packed in the target site X such that a volume of interstitial spaces between the elements 20 is greater than the amount of the fluent material 22 delivered to the target site X. This may be advantageous to facilitate tissue in-growth in the void spaces.

Examples 1, 2, and 3 may be desirable for different applications. Each of the examples can be achieved by using the disclosed low pressure design principles to select the volume of fluent material 22 delivered versus the volume of the elements 20 delivered and by analyzing the packing factors of the geometries of the selected elements 20. Thus, the system 10 can be designed to achieve desired delivery pressures of the fluent material 22 in the vertebral body 12.

The volumetric ratio may be modified by varying the outer diameter OD of the elements 20, the inner diameter ID of the delivery passage 34 and/or the minimum dimension T of the push rod 24. Additionally, the volumetric ratio may be controlled by controlling the volume of the fluent material 22 disposed within the void spaces 63.

Therefore, the system 10 may be customized to change the volumetric ratio of the elements 20 to the fluent material 22 delivered to the target site X to create the final implant M, as shown in FIGS. 26A-26C. Additionally, the user can control advancement of the elements 20, while the fluent material 22 is supplied in a dependent relationship to the advancement of the elements 20, as illustrated in FIG. 25. This relationship may also be variable, selectable, or independent of element 20 advancement to allow user input to control the volume of the fluent material 22 delivered relative to the volume of the elements 20 delivered, as illustrated in FIG. 21.

Figures 27D, 27E:
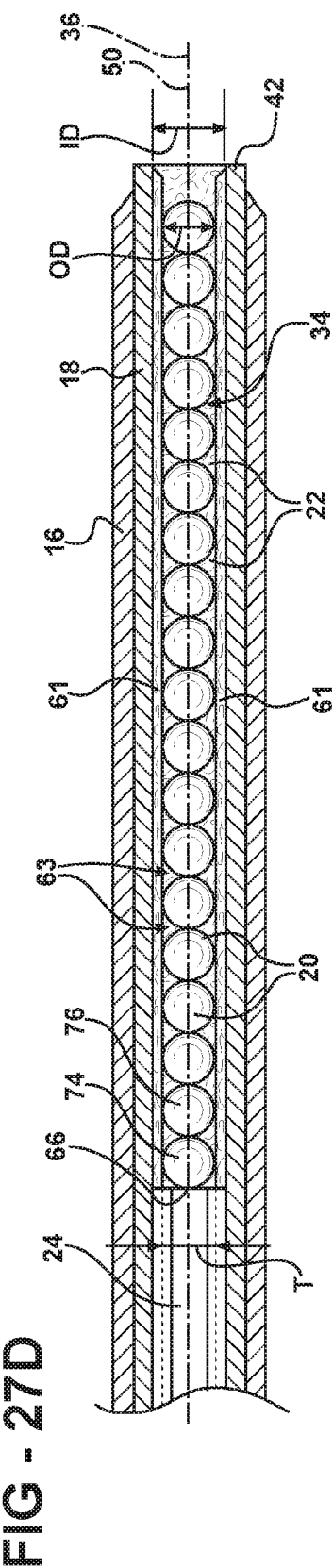

FIGS. 27A-27E illustrate different methods of varying a volumetric ratio of the elements 20 to the fluent material 22. It should be appreciated that the elements 20 and the fluent material 22 are preferably delivered to the interior of the vertebral body 12 at a volumetric ratio of the elements 20 to the fluent material 22 of from about 0.1:1 to about 10:1. More preferably, the elements 20 and the fluent material 22 are delivered at a volumetric ratio of about 2:1 to about 5:1. Most preferably, the elements 20 and the fluent material 22 are delivered at a volumetric ratio about 2:1. This occurs, for example, when the outer diameter OD of the elements 20 and the outer diameter of the push rod 24 is substantially equal to the inner diameter ID of the delivery cannula 18 and the fluent material 22 has a high viscosity, as shown in FIG. 27A.

Referring again to FIG. 27A, the elements 20 fit tightly within the delivery cannula 18. Additionally, the elements 20 are disposed adjacent one another and define the void spaces 63 therebetween. The volumetric ratio of 2:1 is achieved because the volume of elements 20 is twice the volume of the void spaces 63.

Using spherical elements 20 for illustration, the three primary variables involved in controlling these ratios include the outer diameter OD of the elements 20, the minimum dimension T of the push rod 24, and the volume of the fluent material 22 disposed in the void spaces 63, as discussed above. By varying one or more of these variables, the volume of the elements 20 delivered to the target site X, relative to the volume of the fluent material 22 delivered to the target site X, to form the implant M can be controlled. The variables and calculations used to customize the final implant M geometry will vary depending on the geometry of the delivery cannula 18, the push rod 24, and the elements 20. The following three examples assume a cylindrical push rod 24 and delivery passage 34 and a spherical element 20 where the inner diameter ID of the delivery cannula 18 and the outer diameter OD of the spherical element 20 are held constant with only the minimum dimension T of the push rod 24 being varied. Also, these examples are approximations and assume that a unit length movement of the push rod 24 displaces an equal volume of the mixture of the elements 20 and the fluent material 22 that are disposed in the path of the push rod 24. Therefore, the fluent material 22 that is carried by the elements 20 through surface tension may not be accounted for. For the purposes of these examples, assume the inner diameter ID of the delivery cannula 18 is 0.114 inches and the outer diameter OD of the spherical elements 20 are 0.083 inches. Thus, in each example, the volume of one element 20 is 2.994 (10E-4) in^3. Each of the following examples is calculated on a section that is equal in length to one element diameter. For purposes of illustration, the embodiment of the delivery cannula 18 shown in FIGS. 27B-27D correspond to the delivery cannula 18 shown in FIGS. 8A-8C.

EXAMPLE 4

As illustrated in FIG. 27B, the minimum dimension T of the push rod 24 is 0.083 inches, which is equal to the outer diameter OD of the spherical elements 20. Thus, the push rod 24 volume per section is 4.491 (10E-4) in^3. The volume of the fluent material 22 delivered per section would be 1.497 (10E-4) in^3 and the ratio of the elements 20 to the fluent material 22 is 2:1.

EXAMPLE 5

As illustrated in FIG. 27C, the minimum dimension T of the push rod 24 is 0.073 inches, which is smaller than the outer diameter OD of the spherical elements 20. Thus, the push rod 24 volume per section is 3.474 (10E-4) in^3. The volume of the fluent material 22 delivered per section would be 4.8 (10E-5) in^3 and the ratio of the elements 20 to the fluent material 22 is 6.25:1. This means that the volume of the fluent material 22 is much less than the volume of the elements 20.

EXAMPLE 6

As illustrated in FIG. 27D, the push rod 24 extends into the grooves 65 and has an effective diameter of 0.098 inches (the cross-section of the push rod 24 is not circular), which is larger than the outer diameter OD of the spherical elements 20. The push rod 24 may be similar to the types shown in FIGS. 15-19. Thus, the push rod 24 volume per section is 6.261 (10E-4) in^3. The volume of the fluent material 22 delivered per section would be 1.497 (3.267E-4) in^3 and the ratio of the elements 20 to the fluent material 22 is 0.91:1. This means that the volume of fluent material 22 is almost equal to the volume of the elements 20.

In FIG. 27E, an example showing elements 20 that have an outer diameter OD which is less than one-half of the inner diameter ID of the delivery cannula 18 is shown. This example merely shows that multiple variations of the minimum dimension T of the push rod 24 and the outer diameter OD of the elements 20, as compared to the inner diameter ID of the delivery cannula 18, may be used to control the volumetric ratio of the elements 20 to the fluent material 22.

Referring again to FIGS. 8A-8C, another method of varying the volumetric ratio of the elements 20 to the fluent material 22 delivered is illustrated. Ideally, the grooves 65 are provided, as discussed above, to fill the voids spaces between the elements 20 and allow for simultaneous delivery of the elements 20 and the fluent material 22 and to also allow the fluent material 22 to backflow around the elements 20 such that pressurization of the fluent material 22 does not occur due to insufficient clearance between the spherical elements 20 and the delivery wall 61. However, it should be appreciated that the grooves 65 are not required for low pressure delivery as the geometry of the elements 20 may be selected to allow backflow, e.g., grooves or passage on the elements 20, or lesser amounts of fluent material 22 may be delivered. Additionally, as discussed above, if the pusher 68 is used, the pusher 68 may define the holes 70 or the gaps 72 between the pusher 68 and the delivery wall 61. Another variable to control (based on the previously defined variables), is the spacing between the push rod 24 and the delivery wall 62 of the delivery cannula 18, noted by "P" on FIGS. 27A-27E. This spacing P, the holes 70, and/or the gaps provide a volume available for the fluent material 22 to backflow into the delivery cannula 18 during use. As a result, this volume can also be used as storage for excess fluent material 22 to further control whether the fluent material 22 is delivered under pressure.

This configuration of internal guide ribs 61 and grooves 65 provides at least two benefits for this system. One benefit is a larger flow area for the fluent material 22 to pass in order to fill the void spaces 63 between the elements 20. When using a fluent material 22 with a relatively high viscosity, loading the fluent material 22 into the void spaces 63 can be difficult when the area between the elements 20 and the delivery wall 62 is small. Another benefit of this configuration is the guide ribs 61 can provide radial support to the elements 20, keeping the elements 20 more axially aligned along the delivery axis 36 in order reduce a radial component of the force transferred to the delivery walls 62. The frictional losses between certain element shapes (e.g. spherical elements) and the delivery cannula 18 would be reduced with better axial alignment and the likelihood of spherical or similar shaped elements to wedge or lodge in the delivery cannula is also reduced.

The invention has been described in an illustrative manner, and it is to be understood that the terminology which has been used is intended to be in the nature of words of description rather than of limitation. Obviously, many modifications and variations of the present invention are possible in light of the above teachings, and the invention may be practiced otherwise than as specifically described.

What is claimed is:

1. A method of delivering elements and a fluent material capable of setting into a hardened condition into a vertebral body having an interior of cancellous bone to form an implant, said method comprising the steps of:
   providing a delivery cannula defining a delivery passage and at least one groove separate from and open to the delivery passage, and a push rod;
   placing the fluent material at least partially within a void space defined among the elements in the delivery passage of the delivery cannula, wherein the elements are disposed adjacent to one another in the delivery passage; and
   inserting the push rod in the delivery passage of the delivery cannula to slide the push rod along the delivery passage and apply a force to a first of the elements and transfer the force through the first element to a second of the elements disposed in the delivery passage to move the elements through the delivery passage and into the interior of the vertebral body such that the fluent material is simultaneously carried with the elements as the elements move through the delivery passage and into the interior of the vertebral body, and such that the fluent material flows from the void space to the at least one groove and backflows around the elements so that pressurization of the fluent material is reduced upon application of the force whereby the fluent material sets to the hardened condition to secure the elements and form the implant.

2. A method as set forth in claim 1 further comprising loading the fluent material into the delivery cannula after the elements are disposed adjacent to one another in the delivery passage.

3. A method as set forth in claim 2, wherein loading the fluent material into the delivery cannula includes attaching a fill container to the delivery cannula and moving the fluent material from the fill container to the delivery cannula so that the fluent material flows around the elements in the delivery passage to at least partially fill in the void space.

4. A method as set forth in claim 3 further comprising sealing an end of the delivery cannula to retain the fluent material within the delivery cannula.

5. A method as set forth in claim 1 further comprising filling a loading cannula with the fluent material and the elements and transferring the fluent material and the elements from the loading cannula to the delivery cannula.

6. A method as set forth in claim 1 further comprising attaching a fill container to the delivery cannula and transferring the fluent material and the elements from the fill container to the delivery cannula.

7. A method as set forth in claim 1 further comprising loading the fluent material into the delivery cannula while a distal containment member holds the elements in the delivery cannula.

8. A method as set forth in claim 7 further comprising removing the distal containment member from the delivery cannula prior to delivering the fluent material and the elements into the vertebral body.

9. A method as set forth in claim 1 further comprising loading the fluent material into a separate delivery passage.

10. A method as set forth in claim 1 further comprising delivering the elements and the fluent material from an exit port radially from the delivery cannula into the interior of the vertebral body.

11. A method as set forth in claim 1, wherein the elements are flexibly connected to one another with a connecting member, said method further comprising moving the access cannula to sever the connecting member with a cutter disposed on a distal end of the access cannula.

12. A method as set forth in claim 1 further comprising measuring a linear distance the push rod travels along the delivery passage of the delivery cannula and estimating a volume of the elements and the fluent material delivered into the interior of the vertebral body based on the linear distance the push rod traveled.

13. A method as set forth in claim 1 further comprising controlling a volumetric ratio of the elements to the fluent material to deliver the fluent material at a desired pressure.

14. A method as set forth in claim 13 further comprising delivering the elements and the fluent material at a volumetric ratio of the elements to the fluent material of from 0.1:1 to 10:1.

15. A method as set forth in claim 13 further comprising delivering the elements and the fluent material at a volumetric ratio of the elements to the fluent material of from 0.2:1 to 5:1.

16. A method as set forth in claim 13 further comprising delivering the elements and the fluent material at a volumetric ratio of the elements to the fluent material of about 2:1.

17. A method of delivering elements and a fluent material capable of setting into a hardened condition into a vertebral body having an interior of cancellous bone to form an implant, said method comprising the steps of:

providing a delivery cannula, and a push rod including a pusher;

placing the fluent material at least partially within a void space defined among the elements in a delivery passage of the delivery cannula, wherein the elements are disposed adjacent to one another in the delivery passage; and inserting the push rod in the delivery passage of the delivery cannula to slide the pusher along the delivery passage and apply a force to move the elements through the delivery passage and into the interior of the vertebral body such that the fluent material is simultaneously carried with the elements as the elements move through the delivery passage and into the interior of the vertebral body, and such that the fluent material backflows past the pusher so that pressurization of the fluent material is reduced upon application of the force, whereby the fluent material sets to the hardened condition to secure the elements and form the implant.

18. The method as set forth in claim 17 wherein the pusher and the delivery cannula define a gap therebetween such that the fluent material backflows through the gap and around the pusher during the step of inserting the push rod.

19. The method as set forth in claim 17 wherein the pusher defines a hole such that the fluent material backflows through the hole during the step of inserting the push rod.

* * * * *